(12) United States Patent  
Smirnov et al.

(10) Patent No.: US 9,057,704 B2  
(45) Date of Patent: Jun. 16, 2015

(54) SERS-SENSOR WITH NANOSTRUCTURED SURFACE AND METHODS OF MAKING AND USING

(75) Inventors: Valery K. Smirnov, Yaroslavl (RU); Dmitry S. Kibalov, Yaroslavl (RU)

(73) Assignee: Wostec, Inc., San Francisco, CA (US)

( * ) Notice: Subject to any disclaimer, the term of this patent is extended or adjusted under 35 U.S.C. 154(b) by 0 days.

(21) Appl. No.: 14/362,398

(22) PCT Filed: Dec. 12, 2011

(86) PCT No.: PCT/RU2011/000977  
§ 371 (c)(1),  
(2), (4) Date: Jun. 2, 2014

(87) PCT Pub. No.: WO2013/089578  
PCT Pub. Date: Jun. 20, 2013

(65) Prior Publication Data  
US 2015/0042988 A1      Feb. 12, 2015

(51) Int. Cl.  
*G01J 3/44*      (2006.01)  
*G01N 21/65*   (2006.01)  
*B81C 1/00*     (2006.01)

(52) U.S. Cl.  
CPC ............ *G01N 21/65* (2013.01); *B81C 1/00031* (2013.01); *G01N 21/658* (2013.01); *G01N 2201/06113* (2013.01)

(58) Field of Classification Search  
CPC ................ G01N 21/65; G01N 21/658; G01N 2021/656; G01J 3/44; G01J 3/02  
USPC ......................................................... 356/301  
See application file for complete search history.

(56) References Cited

U.S. PATENT DOCUMENTS

| 4,009,933 A | 3/1977 | Firester |
| 4,072,541 A | 2/1978 | Meulenberg et al. |
| 4,233,109 A | 11/1980 | Nishizawa |
| 4,400,409 A | 8/1983 | Izu et al. |
| 4,857,080 A | 8/1989 | Baker et al. |
| 5,160,618 A | 11/1992 | Burggraaf et al. |
| 5,498,278 A | 3/1996 | Edlund |
| 5,530,272 A | 6/1996 | Kudo et al. |

(Continued)

FOREIGN PATENT DOCUMENTS

| RU | 2141699 C1 | 11/1999 |
| RU | 2152108 C1 | 6/2000 |

(Continued)

OTHER PUBLICATIONS

International Search Report and Written Opinion for PCT/RU2011/000977 mailed Sep. 6, 2012.

(Continued)

*Primary Examiner* — Tarifur Chowdhury  
*Assistant Examiner* — MD Rahman  
(74) *Attorney, Agent, or Firm* — Lowe Graham Jones PLLC; Bruce E. Black

(57) ABSTRACT

A surface enhanced Raman scattering (SERS) sensor includes a substrate with a nanostructured surface. The nanostructured surface has a quasi-periodic, anisotropic array of elongated ridge elements having a wave-ordered structure pattern, each ridge element having a wavelike cross-section and oriented substantially in a first direction. The sensor also includes a plurality of metal elements disposed, at least in part, on tops of the ridge elements.

20 Claims, 21 Drawing Sheets

(56) References Cited

U.S. PATENT DOCUMENTS

| | | |
|---|---|---|
| 5,652,020 A | 7/1997 | Collins et al. |
| 5,702,503 A | 12/1997 | Tse Tang |
| 5,734,092 A | 3/1998 | Wang et al. |
| 5,753,014 A | 5/1998 | Van Rijn |
| 6,274,007 B1 | 8/2001 | Smirnov et al. |
| 6,417,939 B1 | 7/2002 | Laude |
| 6,452,724 B1 | 9/2002 | Hansen et al. |
| 6,518,194 B2 | 2/2003 | Winningham et al. |
| 6,580,172 B2 | 6/2003 | Mancini et al. |
| 6,667,240 B2 | 12/2003 | Ozaki et al. |
| 6,706,576 B1 | 3/2004 | Ngo et al. |
| 6,810,899 B2 | 11/2004 | Franz et al. |
| 6,954,275 B2 | 10/2005 | Choi et al. |
| 7,001,446 B2 | 2/2006 | Roark et al. |
| 7,175,694 B2 | 2/2007 | Ma et al. |
| 7,265,374 B2 | 9/2007 | Lee et al. |
| 7,338,275 B2 | 3/2008 | Choi et al. |
| 7,384,792 B1 | 6/2008 | Wang et al. |
| 7,453,565 B2 | 11/2008 | Wang et al. |
| 7,604,690 B2 | 10/2009 | Smirnov et al. |
| 7,768,018 B2 | 8/2010 | Smirnov et al. |
| 7,791,190 B2 | 9/2010 | Flores et al. |
| 7,977,252 B2 | 7/2011 | Smirnov et al. |
| 8,426,320 B2 | 4/2013 | Smirnov et al. |
| 8,859,440 B2 | 10/2014 | Smirnov et al. |
| 8,859,888 B2 | 10/2014 | Smirnov et al. |
| 2002/0142704 A1 | 10/2002 | Hu et al. |
| 2002/0154403 A1 | 10/2002 | Trotter |
| 2003/0152787 A1 | 8/2003 | Arakawa et al. |
| 2003/0171076 A1 | 9/2003 | Moloney et al. |
| 2003/0183270 A1 | 10/2003 | Falk et al. |
| 2003/0218744 A1 | 11/2003 | Shalaev et al. |
| 2004/0070829 A1 | 4/2004 | Kurtz et al. |
| 2004/0129135 A1 | 7/2004 | Roark et al. |
| 2004/0174596 A1 | 9/2004 | Umeki |
| 2004/0201890 A1 | 10/2004 | Crosby |
| 2004/0238851 A1 | 12/2004 | Flores et al. |
| 2005/0046943 A1 | 3/2005 | Suganuma |
| 2006/0205875 A1 | 9/2006 | Cha et al. |
| 2006/0230937 A1 | 10/2006 | Smirnov et al. |
| 2006/0273067 A1 | 12/2006 | Smirnov et al. |
| 2007/0012355 A1 | 1/2007 | LoCascio et al. |
| 2007/0082457 A1 | 4/2007 | Chou et al. |
| 2008/0072958 A1 | 3/2008 | Dutta |
| 2008/0119034 A1 | 5/2008 | Smirnov et al. |
| 2009/0118605 A1 | 5/2009 | Van Duyne et al. |
| 2009/0162966 A1 | 6/2009 | Jawarani et al. |
| 2010/0171949 A1 | 7/2010 | Mazur et al. |
| 2010/0300893 A1 | 12/2010 | Suh et al. |
| 2011/0232744 A1 | 9/2011 | Larsen et al. |
| 2011/0248386 A1 | 10/2011 | Smirnov et al. |
| 2014/0151715 A1 | 6/2014 | Smirnov et al. |
| 2014/0352779 A1 | 12/2014 | Smirnov et al. |
| 2015/0042988 A1 | 2/2015 | Smirnov et al. |

FOREIGN PATENT DOCUMENTS

| | | |
|---|---|---|
| RU | 2173003 C2 | 8/2001 |
| RU | 2180885 C1 | 3/2002 |
| RU | 2204179 C1 | 5/2003 |
| RU | 2231171 C1 | 6/2004 |
| RU | 2240280 C1 | 11/2004 |
| RU | 2321101 C1 | 3/2008 |
| TW | 200939471 A | 9/2009 |
| WO | 0017094 | 3/2000 |
| WO | 2005050697 A2 | 6/2005 |
| WO | 2010072862 | 7/2010 |
| WO | 2011044687 | 4/2011 |
| WO | 2012009467 | 1/2012 |

OTHER PUBLICATIONS

International Search Report and Written Opinion for International Patent Application No. PCT/RU2011/000489 mailed Mar. 1, 2012.

International Search Report and Written Opinion for International Patent Application No. PCT/RU2011/000631 mailed Mar. 1, 2012.

International Search Report and Written Opinion for International Patent Application No. PCT/RU2011/00594 mailed Apr. 19, 2012.

International Search Report and Written Opinion for International Patent Application No. PCT/US2006/011420 mailed Jun. 26, 2008.

International Search Report and Written Opinion for International Patent Application No. PCT/US2006/021564 mailed Jul. 28, 2008.

Karen, A. et al., "Quantitative Investigation Of The O2+-Induced Topography of GaAs and Other III-V Semiconductors: an STM Study of the Ripple Formation and Suppression of the Secondary Ion Yield Change by Sample Rotation," Surface and Interface Analysis, vol. 23, 1995, pp. 506-513.

Scott, K.L. et al., "Pattern Generators and Microcolumns for Ion Beam Lithography," Journal of Vacuum Science Technology B, 18(6) 2000, pp. 3172-3176.

Vajo, J.J. et al., "Influence of O2+ Energy, Flux, and Fluence on the Formation and Growth of Sputtering-Induced Ripple Topography on Silicon," Journal of Vacuum Science and Tecnology A. 14(5), 1996, pp. 2709-2720.

Official Communication for U.S. Appl. No. 11/421,384 mailed Aug. 21, 2008.

Official Communication for U.S. Appl. No. 11/421,384 mailed Apr. 24, 2009.

Official Communication for U.S. Appl. No. 11/421,384 mailed Sep. 3, 2009.

Official Communication for U.S. Appl. No. 13/164,387 mailed Sep. 6, 2012.

Official Communication for U.S. Appl. No. 13/407,615 mailed Mar. 28, 2014.

European Search Report for European Application No. 06851545.1 mailed Feb. 8, 2010.

Official Communication for U.S. Appl. No. 13/859,442 mailed Oct. 18, 2013.

Official Communication for U.S. Appl. No. 13/859,442 mailed May 2, 2014.

Official Communication for U.S. Appl. No. 13/859,442 mailed Mar. 27, 2014.

Official Communication for U.S. Appl. No. 11/100,175 mailed Oct. 24, 2007.

Official Communication for U.S. Appl. No. 11/100,175 mailed May 16, 2008.

Official Communication for U.S. Appl. No. 11/100,175 mailed Feb. 9, 2009.

Chapter 7 in the book Sputtering by Particle Bombardment II: Sputtering of Alloys and Compounds, Electron and Neuron Sputtering, Surface Topography, Edited by R. Behrisch, 1983, Springer-Verlag, Berlin-Heidelberg-New York-Tokyo.

Mishra et al. Effect of initial target surface roughness on the evolution of ripple topography induced by oxygen sputtering of Al films, Journal of Applied Physics, vol. 105, 2009, 7 pages.

International Search Report and Written Opinion for PCT/RU2012/000016 mailed Sep. 13, 2012.

International Search Report and Written Opinion for PCT/RU2012/000210 mailed Dec. 20, 2012.

International Search Report and Written Opinion for PCT/RU2014/000458 mailed Feb. 5, 2015.

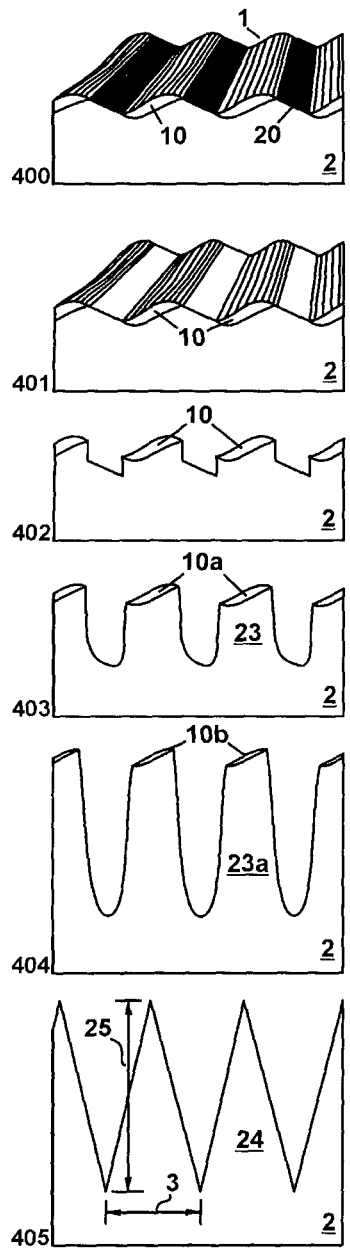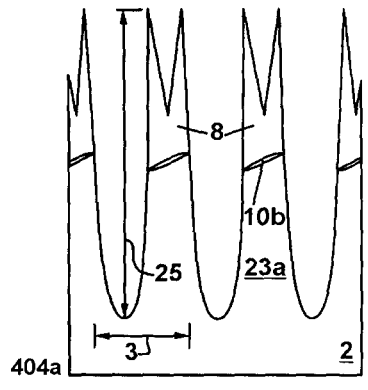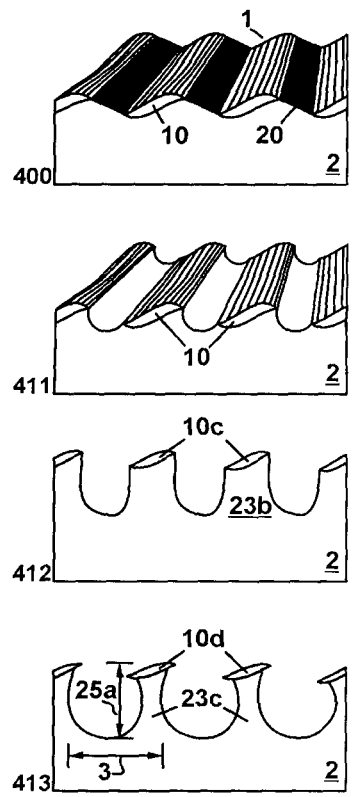
FIG. 2A
FIG. 2B
FIG. 2C

US 9,057,704 B2

SERS-SENSOR WITH NANOSTRUCTURED SURFACE AND METHODS OF MAKING AND USING

CROSS-REFERENCE TO RELATED APPLICATIONS

This present application is a U.S. national stage application of PCT Application No. PCT/RU2011/000977, filed Dec. 12, 2011, which is hereby incorporated by reference in its entirety.

FIELD

The invention relates to the field of optical sensors for detecting and measuring the traces of organic compounds by the method of Raman spectroscopy using the effect of surface enhanced Raman scattering (SERS). The invention also relates to the technology of forming nanostructured elements on the surface of substrates for optical sensors (SERS-sensors) for measuring Raman scattering signal from analyte molecules positioned on the nanostructured surface of the sensor.

BACKGROUND

There is a general interest in the manufacture and use of optical sensors (SERS-sensors) with nanostructured metal surface. FIG. 16A illustrates one type of conventional SERS-sensor with nanostructured metal coverage. This SERS-sensor includes a substrate 161 of copper or silicon oxide, a dense hexagonal array of nanospheres 162 of polystyrene or silicon oxide arranged on the substrate surface, and a metal film 28 over the array of nanospheres (U.S. Patent Application Publication No. 2009/0118605, incorporated herein by reference). The diameter of the nanospheres is 390 nm and the thickness of metal film of silver is 200 nm. This reference also discloses examples of conventional SERS-sensors with a hexagonal array of metal triangles on the surface of the substrate. These sensors can be manufactured by nanosphere lithography (NSL) in which a monolayer of nanospheres is deposited on a substrate surface with dense hexagonal packing, metal is then deposited through the nanospheres, and then the nanospheres are removed. Disadvantages of the NSL method can include low throughput and difficulties in forming large area substrates. Disadvantages of conventional SERS-sensors can include a low surface density of the nanospheres and metal triangles in the arrays and small array sizes which may not surpass a few millimeters.

One type of conventional optical sensor is disclosed in U.S. Pat. No. 7,453,565, incorporated herein by reference. This SERS-sensor is illustrated in FIG. 16B and has a substrate 162 of aluminum, a template of nanopores in anodic aluminum oxide (AAO) 163, and silver nanoparticles 29 deposited in the nanopores of the AAO template. Between the nanoparticles 29 there are the gaps 14. Disadvantages of methods of manufacturing SERS-sensors based on AAO templates can include low throughput, difficulties in forming AAO templates of large area, and instability of the process of forming AAO templates induced by small deviations of critical parameters. A disadvantage of the conventional SERS-sensor can include a small size of the AAO template which may not surpass a few centimeters.

BRIEF SUMMARY

One embodiment is a surface enhanced Raman scattering (SERS) sensor including a substrate with a nanostructured surface. The nanostructured surface has a quasi-periodic, anisotropic array of elongated ridge elements having a wave-ordered structure pattern, each ridge element having a wave-like cross-section and oriented substantially in a first direction. The sensor further includes a plurality of metal elements disposed, at least in part, on tops of the ridge elements.

Another embodiment is a method of making a SERS sensor. The method includes irradiating a surface of a wafer with a first oblique beam of nitrogen ions in a first plane of incidence of the nitrogen ions to form a primary nanomask. The primary nanomask includes a quasi-periodic, anisotropic array of elongated elements having a wave-ordered structure pattern and a wave-like cross-section with wave crests that are substantially perpendicular to the first plane of incidence of the nitrogen ions. The method further includes etching the surface of the wafer with the primary nanomask to generate a nanostructured surface corresponding to the primary nanomask.

The method may further include irradiating the surface of the primary nanomask with a second oblique beam of nitrogen ions in a second plane of incidence of the nitrogen ions, the second plane being rotated around a normal of the wafer surface by an azimuthal angle with respect to the first plane, to form a secondary nanomask. The secondary nanomask includes a quasi-periodic, anisotropic array of elongated elements having a wave-ordered structure pattern and a wave-like cross-section with wave crests that are substantially perpendicular to the second plane of incidence of the nitrogen ions.

The method may also include depositing metal elements over the nanostructured surface.

Yet another embodiment is a nanostructured arrangement including a substrate with a nanostructured surface. The nanostructured surface has a quasi-periodic, anisotropic array of elongated ridge elements having a wave-ordered structure pattern, each ridge element having a wavelike cross-section and oriented substantially in a first direction. In this arrangement the wave-ordered structure pattern is a fragmented wave-ordered structure pattern formed by sequential ion irradiation along two different planes of ion incidence separated by an azimuthal angle in a range of 30 to 90 degrees.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 2A are sequential cross-sectional/perspective views of wavelike ridge elements of a nanostructured surface, as they are formed during a RIE process, according to the invention;

FIG. 2B is a view of a wavelike cross-section of ridge elements of a nanostructured surface resulting from a RIE process, according to the invention;

FIG. 2C are sequential cross-sectional/perspective views of wavelike ridge elements of a nanostructured surface, as they are formed during a wet etch process, according to the invention;

DETAILED DESCRIPTION

The invention relates to the field of optical sensors for detecting and measuring the traces of organic compounds by the method of Raman spectroscopy using the effect of surface enhanced Raman scattering (SERS). The invention also relates to the technology of forming nanostructured elements on the surface of substrates for optical sensors (SERS-sensors) for measuring Raman scattering signal from analyte molecules positioned on the nanostructured surface of the sensor.

For example, a SERS-sensor includes a substrate with a nanostructured surface. The nanostructured surface includes an array of ridge elements, which may be formed using a wavelike silicon nitride nanomask. This nanomask is self-formed during the irradiation of the silicon substrate surface by a beam of nitrogen ions. The nanomask is also self-formed during the irradiation of a silicon layer on the substrate surface by a beam of nitrogen ions. As a result of etching of the substrate through the nanomask a dense quasiperiodic anisotropic array of ridge elements forms with substantially equal heights on the substrate surface. Wet etching, reactive ion etching (RIE), ion etching or any combination thereof can be used as etching process.

Figure 5A:
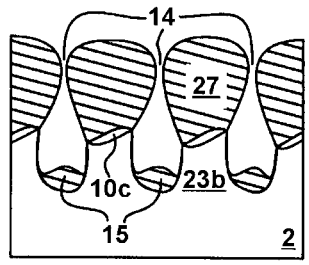
FIGS. 5A to 5E are schematic cross-sectional views of several different embodiments of a SERS-sensor having ridge elements of a nanostructured surface with a wave-ordered structure pattern, according to the invention.

FIG. 5A illustrates one embodiment of a SERS-sensor that includes a substrate 2, for example, of silicon with an array of ridge elements 23b on the substrate surface. The ridge elements 23b have a wavelike cross-section and can be formed as a result of isotropic wet or plasma etching. The tops of the ridge elements 23b can be positioned obliquely with respect to the array plane. The regions 10c of silicon nitride, which make up the nanomask, can be positioned on these tops. Metal nanowires 27 are located on the surface of regions 10c with the gaps 14. Metal nanowires 15 can occur in the trenches between the elements 23b.

Figure 5B:
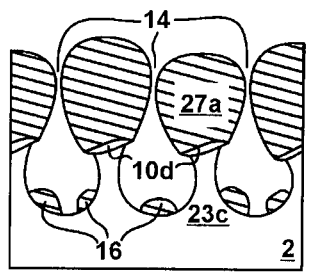

FIG. 5B illustrates an embodiment of a SERS-sensor, in which the size of regions 10d of the nanomask of silicon nitride can exceed the size of the tops of ridge elements 23c and metal islands 16 can occur in nanotrenches between the elements 23c. The ridge elements 23c have a wavelike cross-section and can be formed as a result of isotropic wet or plasma etching. In this embodiment the size of nanowires 27a in cross-section can match that of silicon nitride regions 10d.

Figure 5C:
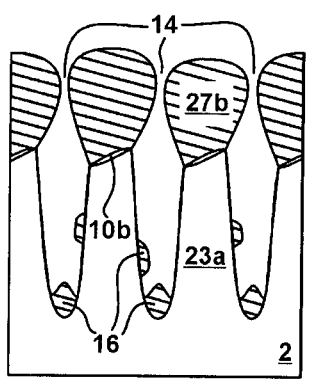

FIG. 5C illustrates an embodiment of a SERS-sensor, in which the ridge elements 23a can have a larger height. The ridge elements 23a have a wavelike cross-section and can be formed as a result of RIE. In this embodiment the size of nanowires 27b in cross-section can match that of silicon nitride regions 10d of the nanomask. It will be understood that the regions 10b, 10c, and 10d are not essential elements of a SERS-sensor and can be lacking.

Figure 5D:
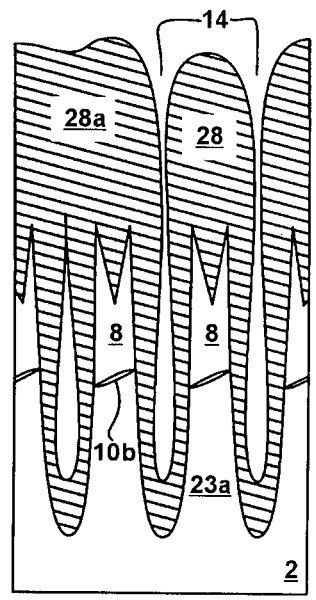

FIG. 5D illustrates an embodiment of a SERS-sensor, in which the ridge elements can have a sawtooth cross-section with concave sidewalls and can be formed as a result of RIE. In this embodiment the bases of the ridge elements include the elements 23a and regions 10b. The tops of the ridge elements are made up of the regions 8 and can be formed in the RIE process from silicon or silicon etch products. The tops of regions 8 can be M-shaped or rounded. In this embodiment the metal coverage can be continuous as shown in FIG. 5D or in the form of nanowires located on tops of the ridge elements and islands located near their bases. There are the gaps 14 between the elements 28 of the metal coverage. Some neighboring elements of the metal coverage can be connected forming the elements 28a.

Figure 5E:
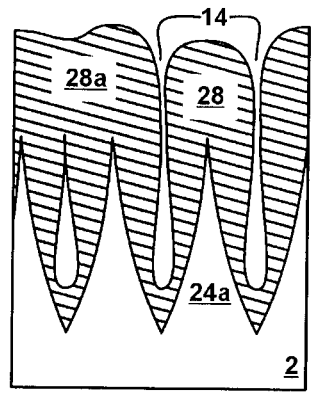

FIG. 5E illustrates an embodiment of a SERS-sensor, in which the ridge elements 24a have a sawtooth cross-section with concave sidewalls and can be formed as a result of RIE and subsequent wet etching of silicon. In this embodiment the metal coverage can be continuous as shown in FIG. 5E or in the form of nanowires located on tops of the ridge elements and islands located near their bases. There are the gaps 14 between the elements 28 of the metal coverage. Some neighboring elements of the metal coverage can be connected forming the elements 28a.

Figure 6A:
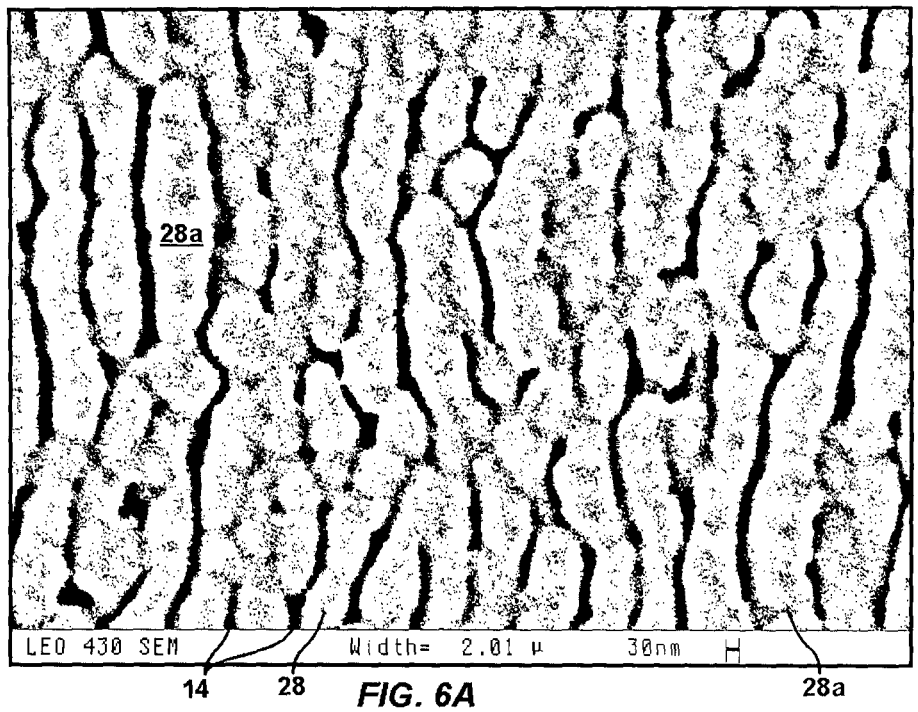
FIGS. 6A to 6B are an SEM top view and an SEM cross-sectional view, angled at 82°, of one embodiment of a SERS-sensor having an array of nanoridges with a period of 90 nm and a silver coverage with a mass-equivalent thickness of 145 nm, according to the invention.

FIG. 6A shows an SEM top view of an embodiment of a SERS-sensor having a substrate with a nanostructured surface, the nanostructured surfaces including an array of nanoridges with a wave ordered structure pattern with a period of about 90 nm and a height of about 150 nm, and a silver coverage with a mass-equivalent thickness of 145 nm. The silver coverage includes elongated elements 28 and elements 28a as shown in cross-section in FIG. 5E.

Figure 6B:
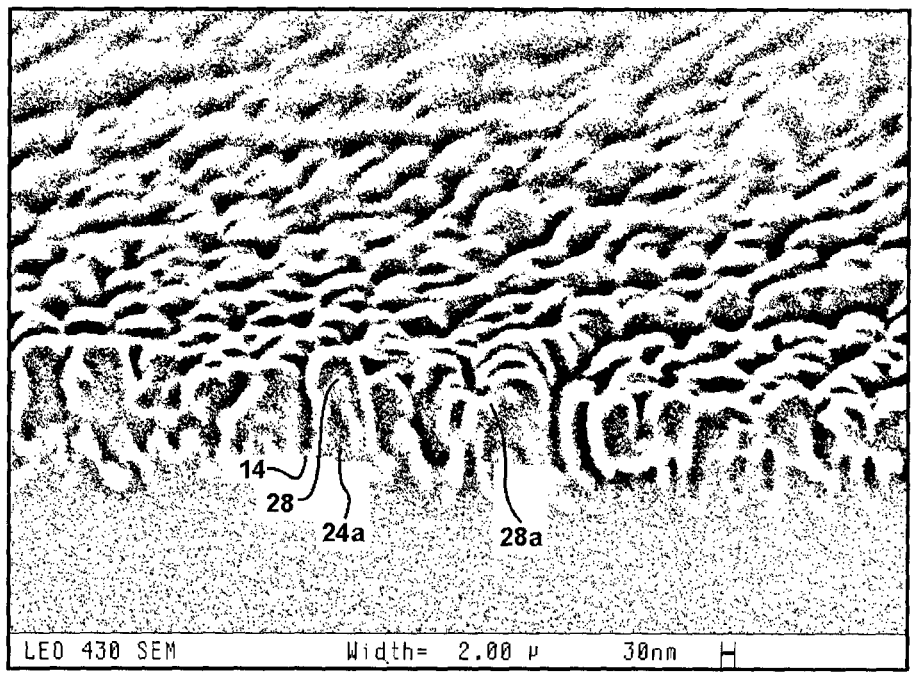

FIG. 6B shows an SEM cross-sectional view, angled at 82°, of an embodiment of a SERS-sensor having an array of nanoridges with a wave ordered structure pattern with a period of about 90 nm and a height of about 150 nm and a silver coverage with a mass-equivalent thickness of 145 nm. On cleavage of a SERS-sensor sample one can observe a ridge element 24a, an element 28 of the silver coverage, a gap 14, and an element 28a of the silver coverage similar to that illustrated in FIG. 5E.

Figure 7A:
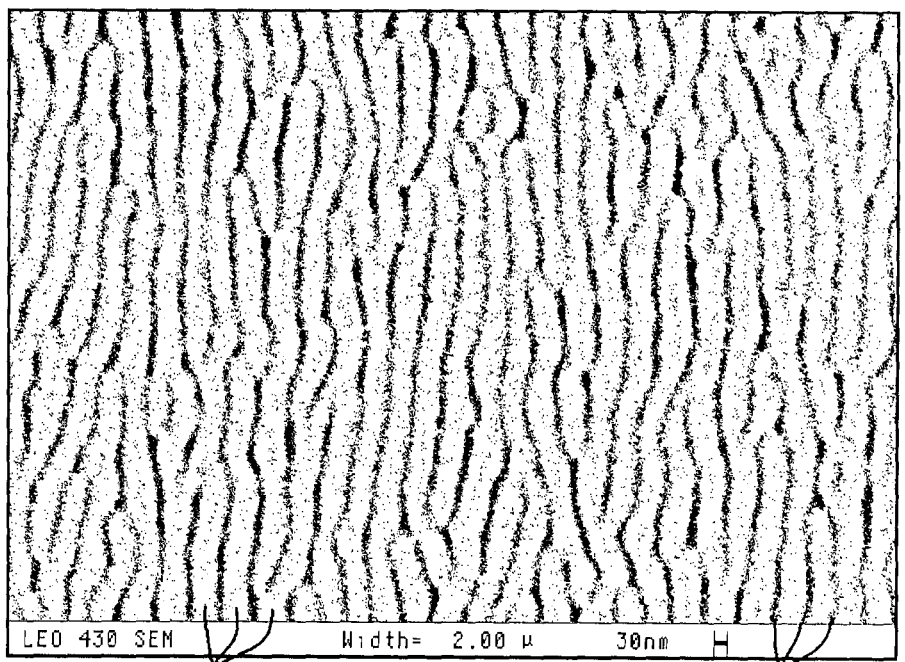
FIGS. 7A to 7B are SEM top views of the embodiments of a SERS-sensor having an array of ridge elements of a nanostructured surface with a period of about 70 and 130 nm, respectively, and a silver coverage having a mass-equivalent thickness of 45 nm, which is composed from an array of silver nanowires positioned on the tops of the ridge elements, according to the invention.

FIG. 7A shows an SEM top view of an embodiment of a SERS-sensor having an array of ridge elements of a nanostructured surface with a wave ordered structure pattern having a period of about 70 nm and a silver coverage with a mass-equivalent thickness of 45 nm, which is composed from an array of silver nanowires 27 positioned on the tops of ridge elements with gaps 14 as shown in cross-section in FIG. 5A.

Figure 7B:
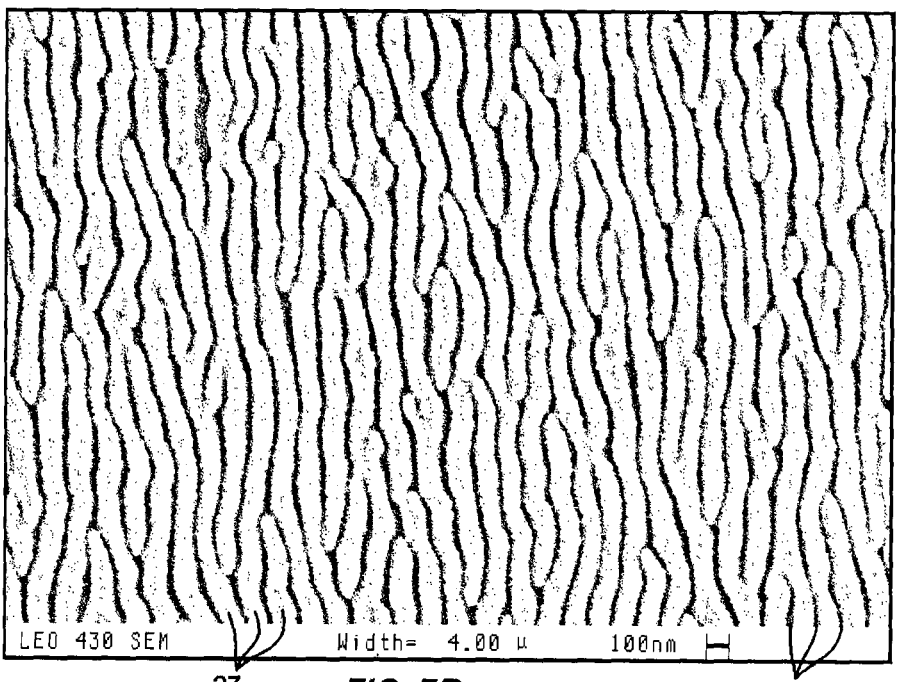

FIG. 7B shows an SEM top view of an embodiment of a SERS-sensor having an array of ridge elements of a nanostructured surface with a wave ordered structure pattern having a period of about 130 nm and a silver coverage with a mass-equivalent thickness of 45 nm, which is composed from an array of silver nanowires 27 positioned on the tops of ridge elements with gaps 14 as shown in cross-section in FIG. 5A.

Figure 9A:
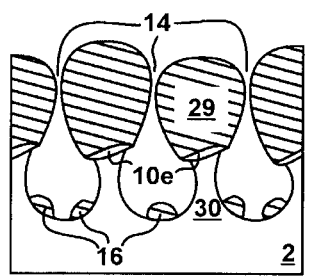
FIGS. 9A to 9D are schematic cross-sectional views of several different embodiments of a SERS-sensor having substantially separated elements of a nanostructured surface with a fragmented wave-ordered structure pattern, according to the invention.

FIG. 9A illustrates another embodiment of a SERS-sensor in which the ridge elements 30 are substantially separated from each other and are mostly columnar elements arranged to match a pattern of a fragmented wave ordered structure. The ridge elements 30 have a wavelike cross-section and can be formed as a result of isotropic wet or plasma etching. The tops of the ridge elements 30 can be positioned obliquely with respect to the array plane. The regions 10e of silicon nitride, which make up the nanomask, can be positioned on the tops of the ridge elements. Metal columnar elements 29 are located on the surfaces of regions 10e with gaps 14. Metal islands 16 can occur between ridge elements 30.

Figure 9C:
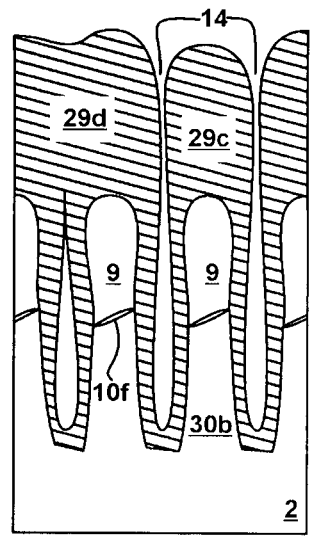
Figure 9B:
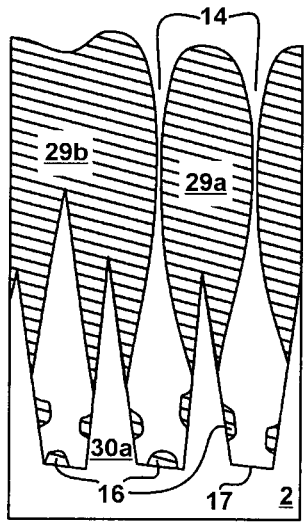

FIG. 9B illustrates an embodiment of a SERS-sensor in which the ridge elements 30a are substantially separated from each other and are mostly nanopeaks arranged to match a pattern of a fragmented wave ordered structure. The ridge elements 30a have a sawtooth cross-section and can be formed as a result of RIE. The columnar metal elements 29a can be positioned on the tops of nanopeaks 30a with gaps 14. Neighboring columnar elements 29a can join each other forming metal elements 29b. Flat areas 17 of the substrate can occur between the nanopeaks 30a.

FIG. 9C illustrates an embodiment of a SERS-sensor in which the ridge elements are substantially separated from each other and are mostly nanopeaks arranged to match a pattern of a fragmented wave ordered structure. The ridge elements have a sawtooth cross-section and can be formed as a result of RIE. In this embodiment the bases of the ridge elements include silicon ridge elements 30b and regions 10f of silicon nitride. The tops of the ridge elements are made up of regions 9 and can be formed in the RIE process from silicon or silicon etch products. In this embodiment the metal coverage can be continuous as shown in FIG. 9C or in the form of columnar elements located on tops of the ridge elements and islands located near their bases. There are gaps 14 between the metal elements 29c. Some neighboring metal elements can be connected forming the metal elements 29d.

Figure 9D:
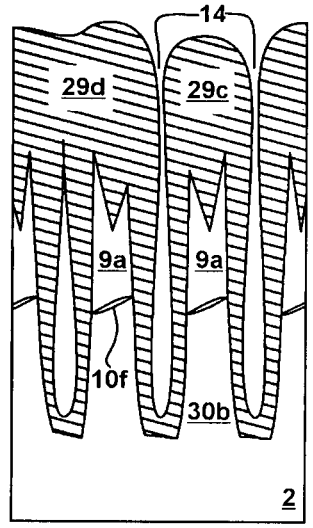

FIG. 9D illustrates an embodiment of a SERS-sensor in which the ridge elements are substantially separated from each other and are mostly nanopeaks arranged to match a pattern of a fragmented wave ordered structure. The ridge elements have a sawtooth cross-section and can be formed as a result of RIE. In this embodiment the bases of the ridge elements include silicon ridge elements 30b and regions 10f of silicon nitride. The tops of the ridge elements are made up of regions 9a which can be M-shaped and can be formed in the RIE process from silicon or silicon etch products. In this embodiment the metal coverage can be continuous as shown in FIG. 9D or in the form of columnar elements located on tops of the ridge elements and islands located near their bases. There are gaps 14 between the metal elements 29c. Some neighboring metal elements can be connected forming the metal elements 29d.

Figure 10A:
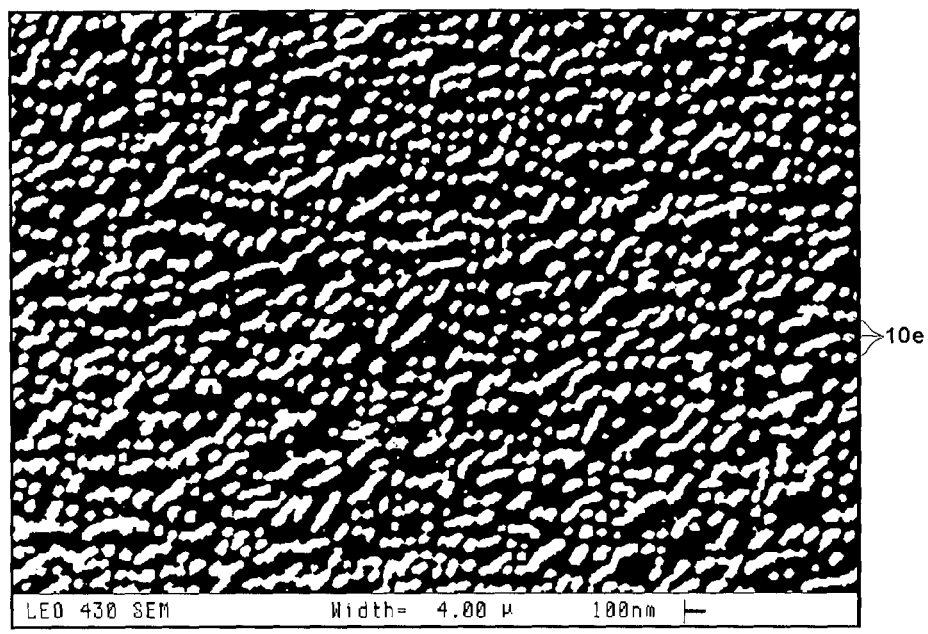
FIG. 10A is a SEM top view of a nanostructured surface having a quasiperiodic anisotropic array of ridge elements with a fragmented wave-ordered structure pattern formed by wet etching, according to the invention.

FIG. 10A is an SEM top view of the nanostructured surface of a silicon substrate with a quasiperiodic anisotropic array of ridge elements which is a plurality of nanopeaks and elongated nanoridges having a pattern of a fragmented wave ordered structure. This array is formed by wet etching of a fragmented nanomask. The average period of this array is about 80 nm. The height of the ridge elements is about 70 nm. Regions 10e of silicon nitride are located on tops of these elements. The elongated nanoridges and ridge elements in the form of nanopeaks are substantially oriented in one direction.

Figure 10B:
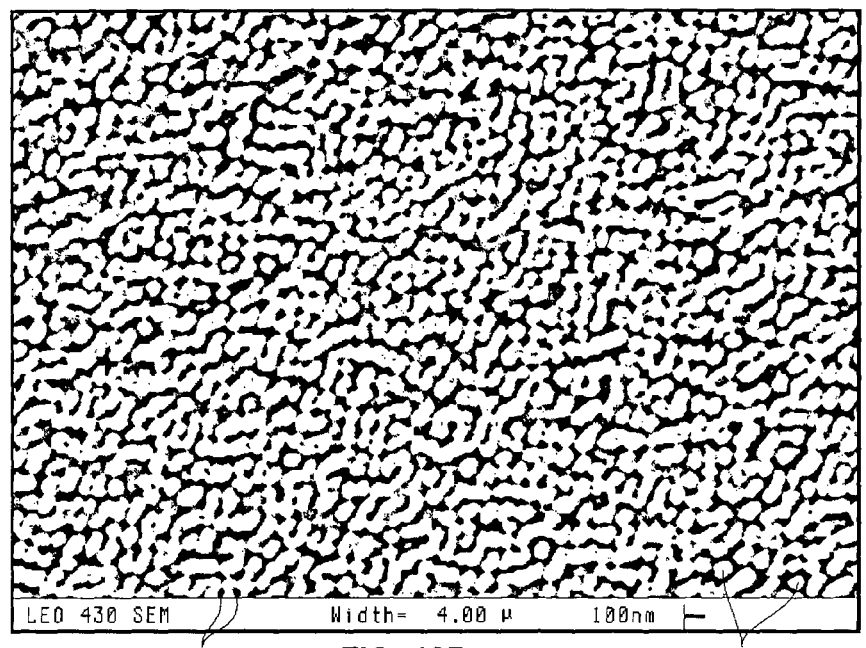
FIG. 10B is a SEM top view of a nanostructured surface having a quasiperiodic anisotropic array of ridge elements with a fragmented wave-ordered structure pattern formed by wet etching and a silver coverage with a mass-equivalent thickness of 70 nm, according to the invention.

FIG. 10B is an SEM top view of an embodiment of a SERS-sensor with the nanostructured surface shown in FIG. 10A and having silver coverage with a mass-equivalent thickness of 70 nm. In this embodiment, the columnar elements 29 of the silver coverage are located on the tops of nanopeaks and have an average diameter of about 100 nm and are shown in cross-section in FIG. 9A.

Figure 11A:
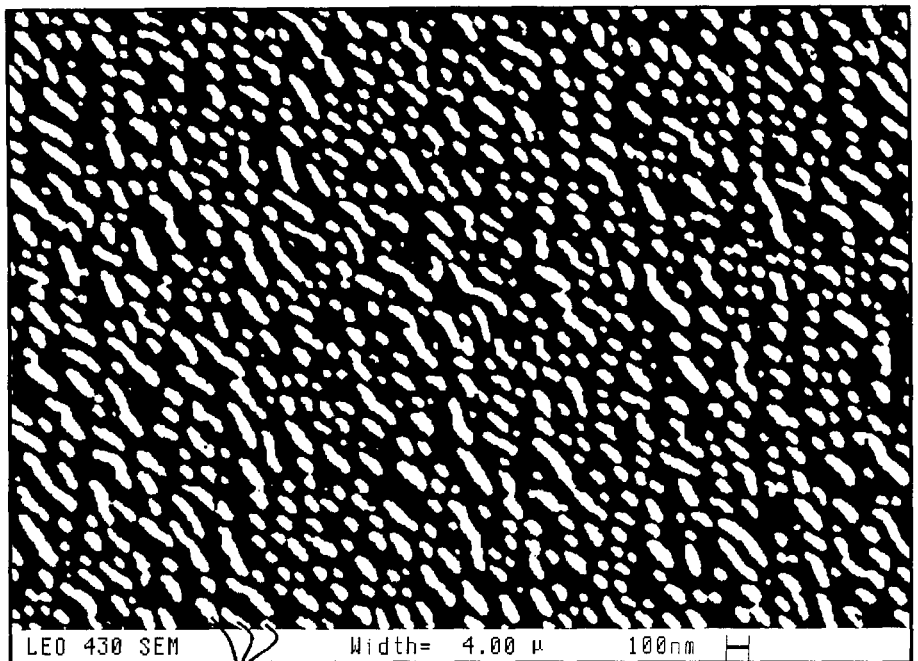
FIG. 11A is a SEM top view of a nanostructured surface having a quasiperiodic anisotropic array of ridge elements with a fragmented wave-ordered structure pattern formed by wet etching and subsequent RIE, according to the invention.

FIG. 11A is an SEM top view of a nanostructured surface of a silicon substrate with a quasiperiodic anisotropic array of ridge elements which is a plurality of nanopeaks and elongated nanoridges with regions 9a on the tops of the nanoridges having a pattern of a fragmented wave ordered structure. This array is formed by RIE of a fragmented nanomask. The average period of this array is about 85 nm. The height of the ridge elements is about 260 nm. The density of the elements is about 5×10 cm. The elongated nanoridges and ridge elements in the form of nanopeaks are substantially oriented in one direction and are shown in cross-section in FIG. 9D.

Figure 11B:
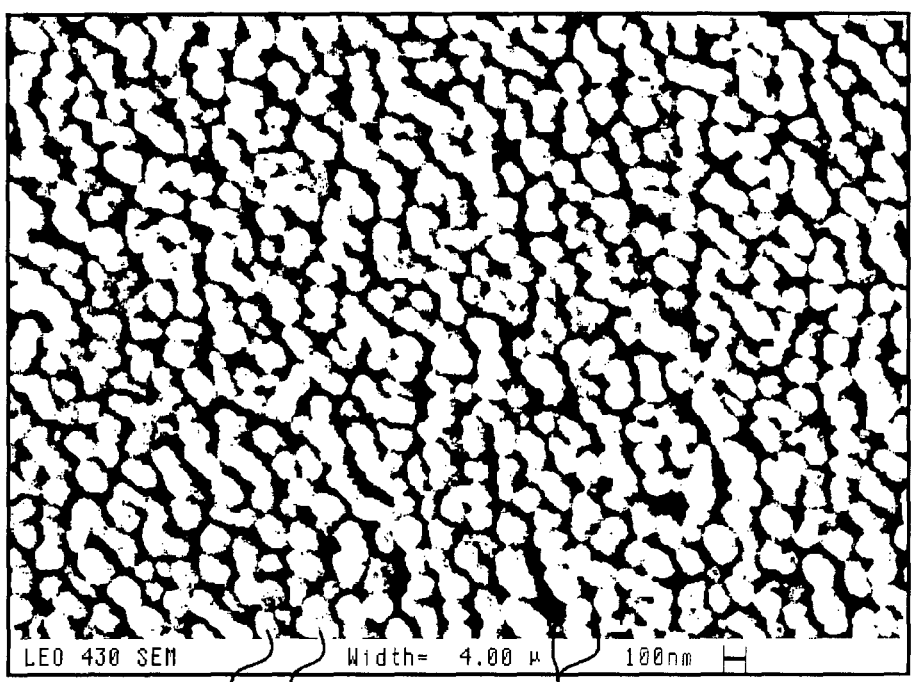
FIG. 11B is a SEM top view of a nanostructured surface having a quasiperiodic anisotropic array of ridge elements with a fragmented wave-ordered structure pattern formed by wet etching and subsequent RIE and a silver coverage with a mass-equivalent thickness of 208 nm, according to the invention.

FIG. 11B is an SEM top view of an embodiment of a SERS-sensor with the nanostructured surface shown in FIG. 11A and having silver coverage with a mass-equivalent thickness of 208 nm. In this embodiment the columnar elements 29c and 29d of the silver coverage are located on the tops of nanopeaks and have an average diameter of about 140 nm and are shown in cross-section in FIG. 9D.

Figure 11C:
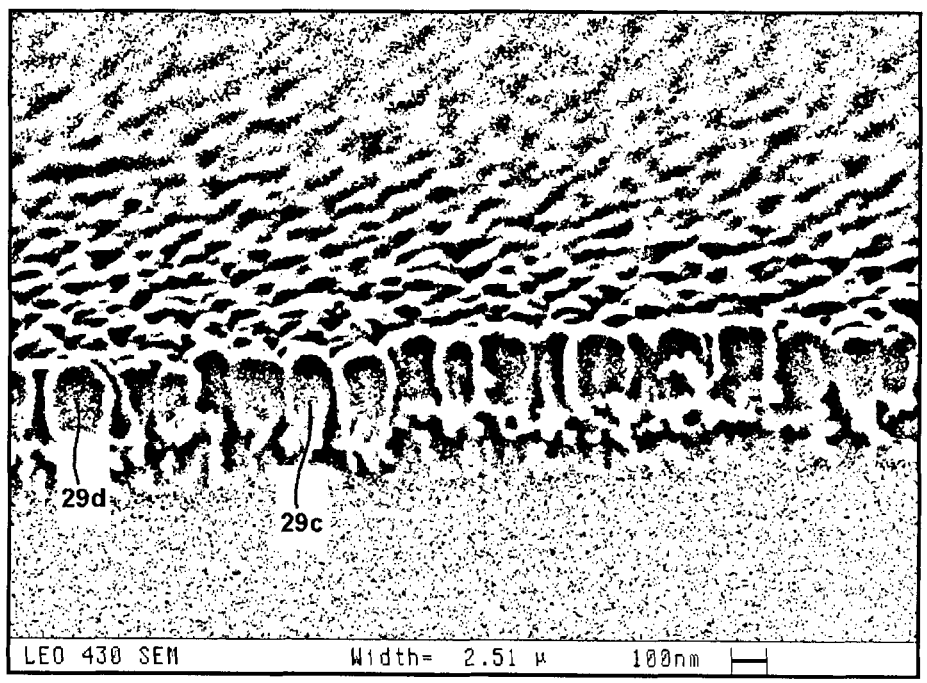
FIG. 11C is an SEM cross-sectional view, angled at 82°, of the embodiment of FIG. 11B, according to the invention.

FIG. 11C is an SEM cross-sectional view, angled at 82°, of the SERS-sensor shown in FIG. 11B. On cleavage of a SERS-sensor sample one can observe columnar elements 29a and 29b of the silver coverage.

One distinctive feature of these embodiments of the SERS-sensor over conventional SERS-sensors is that the size of the nanostructured surface of the substrate can be considerably enlarged compared to the size of the AAO template and the array of nanospheres of conventional SERS-sensors. In at least some embodiments of the present SERS-sensors, the possible size of the nanostructured surface of the substrate is determined by the size of the ion beam. In at least some embodiments, this can be as large as 300 mm.

The embodiments of FIGS. 5A to 5E, 6A and 6B, 7A and 7B, 9A to 9D, 10A to 10C, and 11A to 11C are examples of SERS-sensors. It will be understood that other types of SERS-sensor configurations can be modified to include a nanostructured surface. It will also be understood that the embodiments described above can include a modified nanostructured surface using known etching methods including dry and wet etching. It will also be understood that silicon wafers or wafers of other suitable substrate materials can be used as SERS-substrates and can be nanostructured using a hard nanomask of silicon nitride and known etching methods.

Examples of methods of forming a nanomask on a silicon wafer are described in U.S. Pat. No. 7,768,018 and U.S. Patent Application Publication No. 2008/0119034, both of which are incorporated herein by reference. Examples of ultra thin membranes based on wave-ordered structure patterns are described in U.S. Pat. No. 7,604,690, which is incorporated herein by reference. In at least some embodiments, a wavelike silicon nitride nanomask is formed by irradiation of the surface of a silicon wafer by a beam of nitrogen ions and then etching (e.g., wet etching or reactive ion etching) to create a nanostructured surface of the silicon wafer in the form of a dense quasiperiodic array of nanoridges or nanopeaks. This nanomask can be used for fabricating SERS-sensors from a wafer with a nanostructured surface. In at least some embodiments, the average period of the array is controllably varied in a range from 20 to 150 nm (or 20 to 180 nm or 20 to 200 nm) to increase the performance of SERS-sensors. This process is reliably reproducible and forms a uniform wavelike silicon nitride nanomask, as well as a nanostructure on the surface of wafers of silicon.

In at least some embodiments, a hard nanomask includes a quasi-periodic, anisotropic array of elongated elements having a wave-ordered structure pattern and a wavelike cross-section. At least some of the elements have the following structure in cross-section: an inner region of silicon and a first outer region of silicon nitride covering a first portion of the inner region and being formed from silicon by the nitrogen ion beam. In at least some embodiments, the first outer regions form a net-like or an island-like structure or any combination thereof. In at least some embodiments, the average period of the array is in a range from 20 to 150 nm (or 20 to 180 nm or 20 to 200 nm). In at least some embodiments, the silicon is a solar grade monocrystalline or amorphous silicon.

In at least some embodiments, the nanomask further includes, in cross-section, a second outer region of silicon nitride formed from silicon by irradiation using a nitrogen ion beam. This second outer region covers a second portion of the inner region and connects with the first outer region at a wave crest where the first outer region is substantially thicker than the second outer region. In at least some embodiments, in cross-section the thickness of the second outer region is relatively small or minimal in the middle and increases from the middle towards its borders.

In at least some embodiments, for a beam of nitrogen ions with $N^+$ ions and $N_2^+$ ions in the relative fractions of x and (1−x), respectively, the nanomask average period, the nanomask formation depth, and the ion dose to form the nanomask are (1+x) times greater than those for a $N_2^+$ ion beam. In at least some embodiments, the ion dose for an $N_2^+$ ion beam is in the range $1\times10^{17}$-$5\times10^{17}$ cm$^{-2}$ and the maximum thickness of the first outer region is determined by the formula: $T=2(1+x)E$, where T is the thickness in nm and E is the ion beam energy in keV.

In at least some embodiments, the thickness of the first outer region varies quasi-periodically along the elongated element. In at least some embodiments, the periodic change in thickness of the first outer region along the elongated element is from 50 to 10% of the maximum thickness for a corresponding change in average array period in a range from 20 to 150 nm (or 20 to 180 nm or 20 to 200 nm). In at least some embodiments, the period of change in thickness of the first outer region is greater than or equal to the average array period.

In at least some embodiments, the nanomask is formed by irradiating the silicon surface using an oblique beam of nitrogen ions until a hard nanomask is formed, the nanomask elements being substantially perpendicular to the projection of the ion flow on the silicon surface.

A silicon wafer for a SERS-sensor can be formed with at least one area of nanostructured surface with a nanostructure having a plurality of nanoridges distributed as a quasi-periodic, anisotropic array of silicon nanoridges having a wave-ordered structure pattern and a wave-like cross-section with essentially equal heights and being formed from a hard nanomask. One example of a wave-like cross section is a sawtooth cross-section with sharp tops and bottoms or with sharp tops and flat bottoms, although it will be understood that other wave-like cross sections can be formed. The nanomask includes a quasi-periodic, anisotropic array of elongated elements having a wave-ordered structure pattern and a wavelike cross-section. At least some of the elongated elements have the following structure in cross-section: an inner region of silicon and a first outer region of silicon nitride covering a first portion of the inner region and being formed from silicon by a nitrogen ion beam.

In at least some embodiments, the nanoridges form a net-like or an island-like structure or any combination thereof. In at least some embodiments, the average period of the array of nanoridges is in a range from 20 to 150 nm (or 20 to 180 nm or 20 to 200 nm). In at least some embodiments, the average nanoridge height to average array period ratio is in the range from 0.5 to 5. In at least some embodiments, the wafer is made of silicon or other materials or includes a layer of silicon on the surface.

A silicon wafer for a SERS-sensor can be formed with a nanostructured surface with a plurality of silicon nanopeaks of essentially equal heights arranged as quasi-periodic rows and formed from a hard nanomask. The nanomask includes a quasi-periodic, anisotropic array of elongated elements having a wave-ordered structure pattern and a wavelike cross-section, at least some of the elements having the following structure in cross-section: an inner region of silicon and a first outer region of silicon nitride covering a first portion of the inner region and being formed from silicon by nitrogen ion beam, where the thickness of the first outer region varies quasi-periodically along the element.

In at least some embodiments, the average period of the array is in a range from 20 to 150 nm (or 20 to 180 nm or 20 to 200 nm). In at least some embodiments, the ratio of nanopeak height to the quasi-periodic row period is in the range from 0.5 to 5. In at least some embodiments, the wafer is made of silicon or other materials or includes a layer of silicon on the surface of the wafer.

In at least some embodiments, a SERS-sensor includes a wafer with a nanostructured surface and a coverage of SERS-active metal over the nanostructured surface. In at least some embodiments, the metal coverage includes at least one metal from the group of silver, gold, copper, platinum, palladium, rhodium, ruthenium, osmium, iridium, iron, cobalt, nickel, and aluminum. In at least some embodiments, the SERS-active metal is deposited by methods including, but not limited to, plasma enhanced magnetron sputtering of a metal target, thermal evaporation of metal, or metal deposition from a solution.

One embodiment of a method for nanostructuring the surface of a silicon wafer for a SERS-sensor includes irradiating a surface of the wafer with an oblique beam of nitrogen ions until a hard nanomask is formed. The nanomask includes a quasi-periodic, anisotropic array of elongated elements having a wave-ordered structure pattern and a wavelike cross-section. At least some of the elements have the following structure in cross-section: an inner region of silicon and a first outer region of silicon nitride covering a first portion of the inner region and being formed from silicon by the nitrogen ion beam. The method also includes etching the nanomask and silicon until the nanostructure is formed on the wafer surface.

In at least some embodiments, elongated elements of the hard nanomask extend substantially perpendicular to the projection of the ion flow onto the wafer surface. In at least some embodiments, the ion energy is in the range 0.5-8 keV.

In at least some embodiments, the nanostructure is formed on the surface of the wafer by transferring the topography of a wave ordered structure from a layer of amorphous silicon onto the wafer through plasma etching. (For a general discussion of transferring the topography, see, for example, Smirnov V. K., Kibalov D. S., Method for Shaping Nanotopography on a Film Surface, Russian Patent RU2204179, incorporated herein by reference.) This method includes depositing a layer of amorphous silicon onto a film, sputtering amorphous silicon by a flow of nitrogen ions until a wave-ordered nanostructure is formed in the amorphous silicon layer, transferring a relief of the wave-ordered nanostructure onto a surface of the film by etching the layer of amorphous silicon and the film in plasma. In this case, a wafer of material other than silicon is used as the film. In at least some embodiments, the nanostructured surface of the wafer may include the silicon nitride regions of the wave ordered structure and/or regions of amorphous silicon corresponding to the wave ordered structure pattern.

In at least some embodiments, the hard nanomask is formed as a result of a two stage process. At the first stage a first irradiation of the surface of a wafer is performed with a flux of nitrogen ions in a first plane of incidence of the nitrogen ions to form a primary nanomask. The primary nanomask has a quasi-periodic, anisotropic array of elongated elements with a wave-ordered structure pattern and a wave-like cross-section with wave crests that are substantially perpendicular to the first plane of incidence of the nitrogen ions. Then at the second stage a second irradiation of the surface of the primary nanomask is performed with a flux of nitrogen ions in a second plane of incidence of the nitrogen ions. This second plane is rotated around the wafer surface normal by an azimuthal angle with respect to the first plane to form a secondary nanomask. The secondary nanomask has a quasi-periodic, anisotropic array of elongated elements with a wave-ordered structure pattern and a wave-like cross-section with wave crests that are substantially perpendicular to the second plane of incidence of the nitrogen ions. In at least some embodiments, the azimuthal angle is in the range 30 to 90 degrees. In at least some embodiments, the secondary nanomask is a fragmented wave ordered structure and has separated elements, most of which have an elongation from one half to three times the wavelength of the primary nanomask.

In at least some embodiments, etching associated with the formation of both the nanomask and the array of nanoridges and nanopeaks is performed using a wet method, dry method, or ion beam method, or any combination thereof. In at least some embodiments, the etching is performed by reactive ion etching using a plasma followed by subsequent wet etching.

In at least some embodiments, the nanostructure includes a quasi-periodic, anisotropic array of silicon nanoridges having a wave-ordered structure pattern and a sawtooth cross-section with the nanoridges having essentially equal height. In at least some embodiments, the nanoridges form a net-like or an island-like structure or any combination thereof. In at least some embodiments, the average period of the array of nanoridges is in a range from 20 to 150 nm (or 20 to 180 nm or 20 to 200 nm). In at least some embodiments, the ratio of nanoridge height to the average period of the nanoridges array is in the range from 0.5 to 5.

In at least some embodiments, in cross-section the nanomask further includes a second outer region of silicon nitride being formed from silicon by a nitrogen ion beam. The second outer region covers a second portion of the inner region and connects with the first outer region at a wave crest, where the first outer region is substantially thicker than the second outer region. In at least some embodiments, in cross-section the thickness of the second outer region is relatively small or minimal in the middle and increases from the middle towards its borders. In at least some embodiments, the thickness of the first outer region varies quasi-periodically along the element. In at least some embodiments, the periodic change in thickness of the first outer region along the element is from 50 to 10% of the maximum thickness for corresponding change in element array period in a range from 20 to 150 nm (or 20 to 180 nm or 20 to 200 nm). In at least some embodiments, the period of thickness variations of the first outer region is greater than or equal to the average array period.

In at least some embodiments, the nanostructure includes a plurality of silicon nanopeaks of essentially equal height arranged as quasi-periodic rows and formed from a hard nanomask. In at least some embodiments, the average period between the rows is in a range from 20 to 150 nm (or 20 to 180 nm or 20 to 200 nm). In at least some embodiments, the ratio of nanopeak height to average period between the rows is in a range from 0.5 to 5.

Figure 1A:
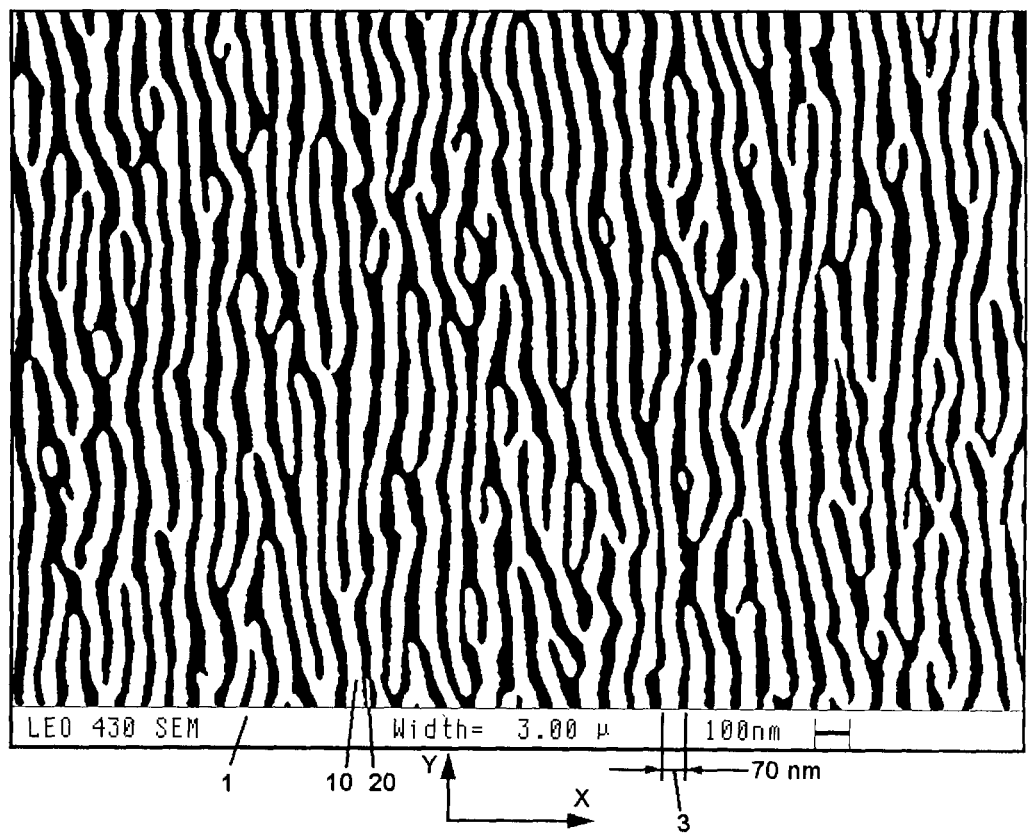
FIG. 1A is a scanning electron microscope (SEM) top view of a nanomask having a period of 70 nm formed on a surface of a silicon wafer using a $N_2^+$ ion beam with energy E=5 keV at an angle of bombardment θ=53° from surface normal, according to the invention.

FIG. 1A shows an SEM image with enhanced contrast (without halftones) of a top view of a self-forming wave ordered structure (WOS). The WOS is a wavelike nanomask 1 with an average period 3 (wavelength $\lambda$=70 nm). The width of the SEM image is equal to 3 μm. White stripes 10 and black stripes 20 are the opposite slopes of the waves of the WOS.

Figures 1B, 1C:
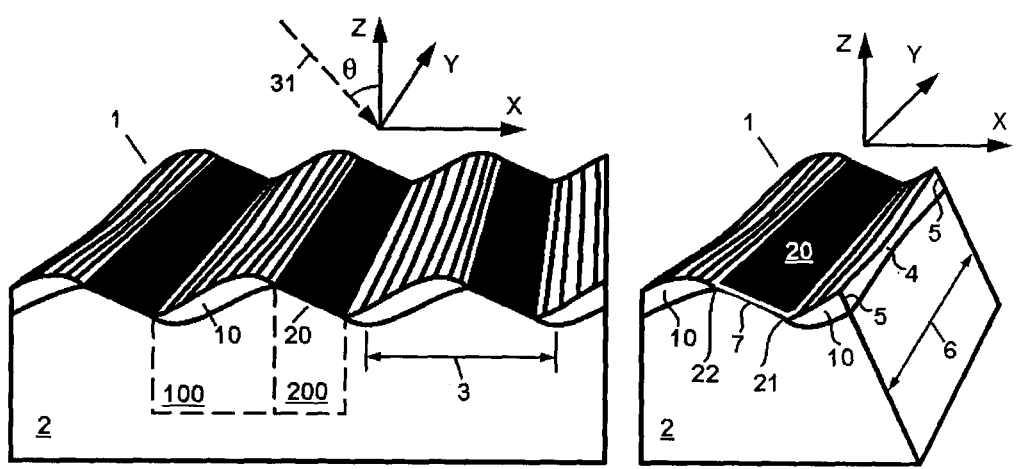
FIG. 1B is a perspective view of elongated elements of a nanomask and their cross-section, according to the invention.
FIG. 1C is a perspective view of elongated elements of a nanomask, their cross-section, and longitudinal section along the element, according to the invention.

FIG. 1B shows a perspective, cross-sectional view of the WOS with a cross section of waves in the XZ plane on the surface of silicon 2. The location of the wave slopes 10 and 20 and their orientation are the same as in FIG. 1A (which corresponds to the XY plane). Wave crests are on average parallel to the Y axis, i.e., the array of waves is anisotropic. A single wave (nanomask element) in the cross-section has an inner region of silicon that includes a first part 100 and a second part 200. The wave also has an outer region of silicon nitride that includes a first part 10 and a second part 20 with a low content of implanted nitrogen atoms. Regions 10 and 20 are formed from silicon by irradiation using a beam of nitrogen ions. In at least some embodiments, the ions of the beam have energy in the range from 0.5 to 8 keV in vacuum during nanomask formation. The regions 10 and 20 are connected to each other at a wave crest or peak. The slopes of the waves of nanomask 1 are preferably tilted symmetrically relative to the XY plane. In some embodiments, the slopes are at an angle of about 30°.

As seen in FIG. 1A, the waves of nanomask 1 have breaks, bends, and branches, i.e. connections with each other. Generally, the waves are elongated along the Y-axis and these elongated elements have a length in the range of, for example, 10$\lambda$ to 30$\lambda$. At the same time there are elements having more or less elongation as well as subwavelength point-like elements with a size of less than $\lambda$. In general, the array of waves is quasiperiodic, the pattern of the waves is uniform, and one can reproduce these arrays with the same average period and the same average elongation of waves under the same conditions of formation. In at least some embodiments, the period is selected from the range from 20 to 150 nm, or 20 to 180 nm or 20 to 200 nm. A distinctive feature of the wavelike nanomask is that its pattern does not contain repeating parts with the same relative positions of the elements, which is due to the self-forming nature of the nanomask.

A characteristic feature of the topology of nanomask 1 in FIG. 1A is that the regions 10 of some elements are connected to each other, and regions 20 of some elements are also connected to each other, to form a branched structure or a mesh. At the same time there are both separated regions 10 and separated regions 20.

FIG. 1C shows one embodiment of a cross section of a region 10 in its center along the Y-axis, i.e. along the wave in the plane perpendicular to the surface of region 10. In at least some embodiments, the thickness of the region 10 varies along the wave from its thinnest part 4 to thickest parts 5 with a period 6. The maximum thickness of region 10 for a beam of nitrogen ions, with $N^+$ ions and $N_2^+$ ions in the relative fractions of x and (1−x), respectively, is determined, in at least some embodiments, by the formula: T=2(1+x)E, where T is the thickness, nm, and E is the ion beam energy, keV. For atomic nitrogen ions $N^+$, the maximum thickness of the first outer region is two times greater than that for molecular ions $N_2^+$. The nanomask period and its formation depth for the ions $N^+$ are also two times higher than those for the ions $N_2^+$. Beams of $N^+$ ions with energy E/2 and $N_2^+$ ions with energy E form nanomasks with the same average periods and the same thicknesses of the first outer regions at the same formation depths. Thus, for a $N^+/N_2^+$ ion beam the average period ($\lambda$) of the nanomask, the thickness of its first outer region (T), the depth of its formation with low wave amplitude ($D_m$), the depth of its formation with grown (saturated) wave amplitude ($D_F$), and the ion doses for corresponding depths of ion sputtering are (1+x) times greater than those values for the pure $N_2^+$ ion beam. In at least some embodiments, the nanomask is formed by the $N_2^+$ ion beam in the ion dose range $5\times10^{16}$-$5\times10^{17}$ cm$^{-2}$. It may be preferable for the $N_2^+$ ion beam to use the dose range $1\times10^{16}$-$5\times10^{17}$ cm$^{-2}$. The given regularities are necessary for using industrial ion sources having mixed beams of $N^+$ and $N_2^+$ ions to form nanomasks on silicon wafers.

Periodic changes may occur in the thickness of the region 10 along the wave and such change may range from, for example, 50 to 10% of its maximum thickness for the corresponding change in the average period 3 of the array. In some embodiments, the average array period is in the range from 20 to 150 nm (or 20 to 180 nm or 20 to 200 nm). For example, the longer the average period 3, the smaller the relative change in the thickness of region 10. When the nanomask period decreases the relative periodic changes in the thickness of the first outer region along the array elements increases: periodic variation in thickness of the first outer region along the element is from 10 to 50% of its maximum thickness when the array period decreases in the range from 150 to 20 nm (or 180 to 20 nm, or 200 to 20 nm). In at least some embodiments, increasing the average period 3 of the array proportionally increases the thickness of region 10. An average period 6 of the change in thickness of region 10 can be equal to or greater than the average period 3 of the array. Regions 10 in the XZ section plane at the borders 21 and 22 may have a beak-like shape. In at least some embodiments, the thickness of regions 20 in cross-section in XZ plane is smallest at the middle point 7 between the borders 21 and 22 and gradually increases towards the borders 21 and 22.

The nanomask shown in FIGS. 1A to 1C can be formed on the silicon surface by irradiation of the silicon with a beam of nitrogen ions $N_2Z$. In one example, the nanomask is formed using a beam having energy of 5 keV and directed in the XZ plane of incidence along the arrow 31 at an angle $\theta$=53° from Z-axis. The projection of ion flow 31 on the XY plane is along the X-axis in this example.

During sputtering of silicon by nitrogen ions a self-forming process takes place resulting in the formation of wavelike nanomask 1. In one example, the depth of sputtering $D_F$=100 nm from the initial level of the silicon surface. In the example, the regions 10 are bombarded by nitrogen ions at near normal angles, and regions 20 are bombarded at glancing angles, which determines the thickness of the regions 10 and 20. Crests of nanomask waves in an array can be predominantly oriented perpendicular to the projection of ion flow on the surface of silicon, (e.g., perpendicular to the X-axis when the ion flow projection is along the X-axis). In at least some embodiments, with decreasing ion energy and increasing ion bombardment angle $\theta$ measured from surface normal (Z-axis) the wavelength $\lambda$ or period 3 of the array can be reduced.

Ion energy can range from, for example, 0.5 to 4 keV for $N^+$ ions and from, for example, 1 to 8 keV for $N_2^+$ ions. Such energy ranges may result in a nanomask period in the range from 20 to 150 nm (or 20 to 180 nm or 20 to 200 nm). In at least some embodiments, the topology of the nanomask 1 does not change for bombardment angles in the range $\theta$=50° to 55°. With ion energies greater than 8 keV and using $N_2^+$ ion beam, one can form the nanomasks with the periods larger than 150, 180 or 200 nm.

Figure 1D:
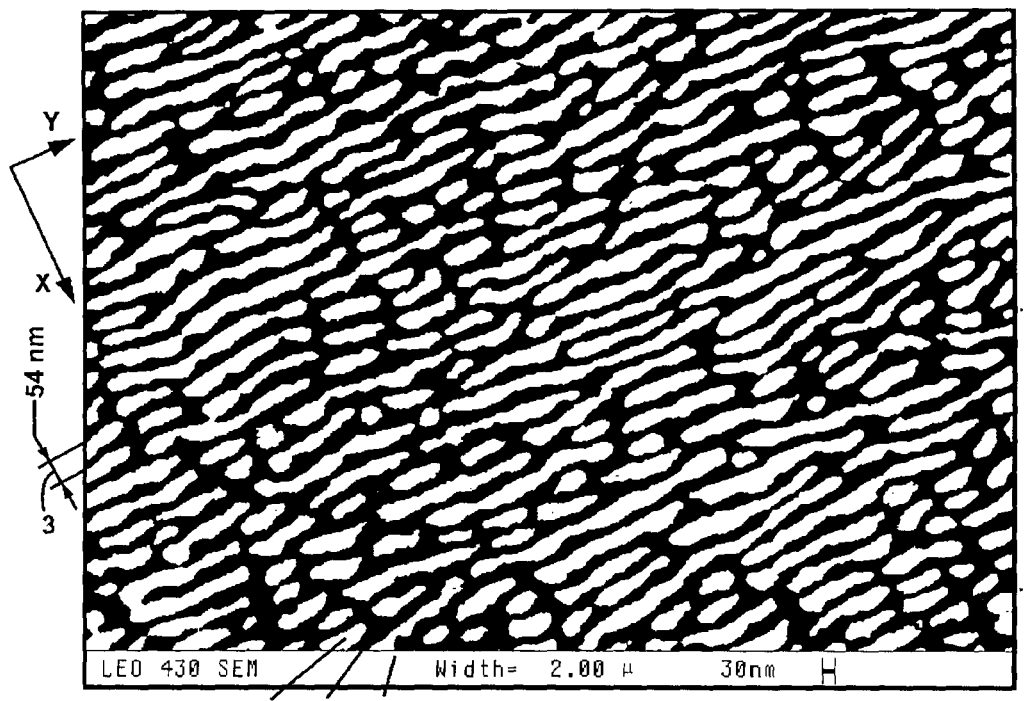
FIG. 1D is a SEM top view of a nanomask with a period of 54 nm formed on a surface of a silicon wafer using a $N_2^+$ ion beam at E=4 keV, θ=59°, according to the invention.
Figure 1E:
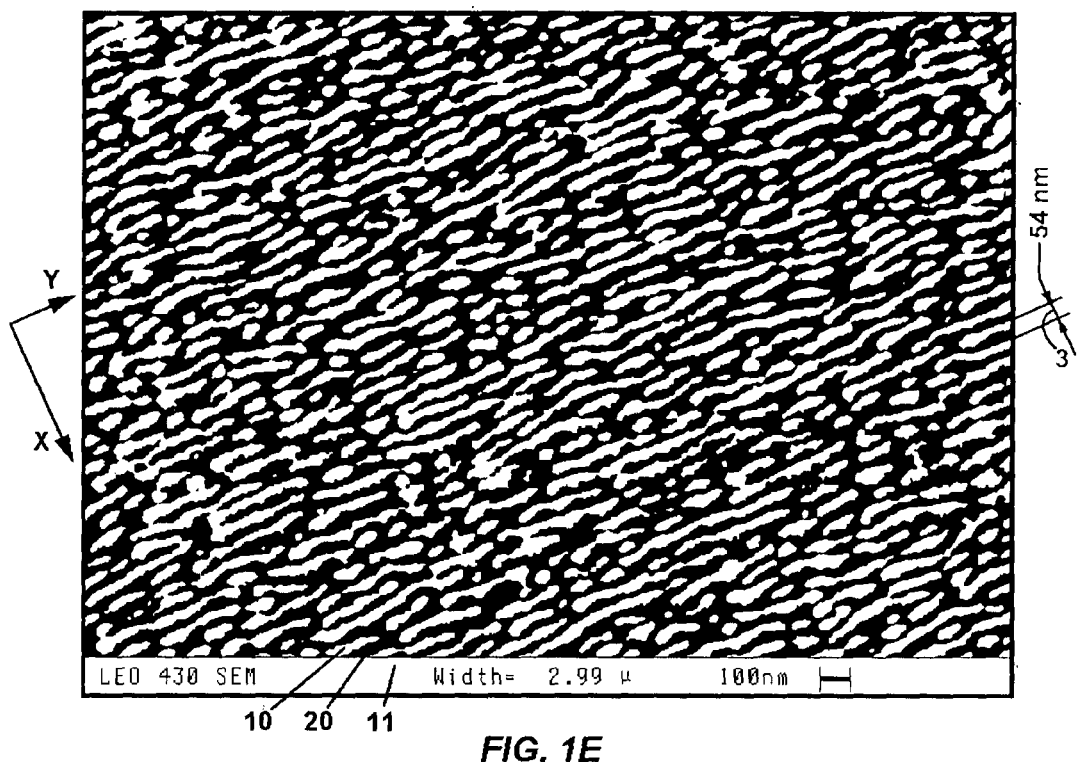
FIG. 1E is a SEM top view of a nanomask with a period of 54 nm formed on a surface of a silicon wafer using a $N_2^+$ ion beam at E=6 keV, θ=63°, according to the invention.
Figure 1F:
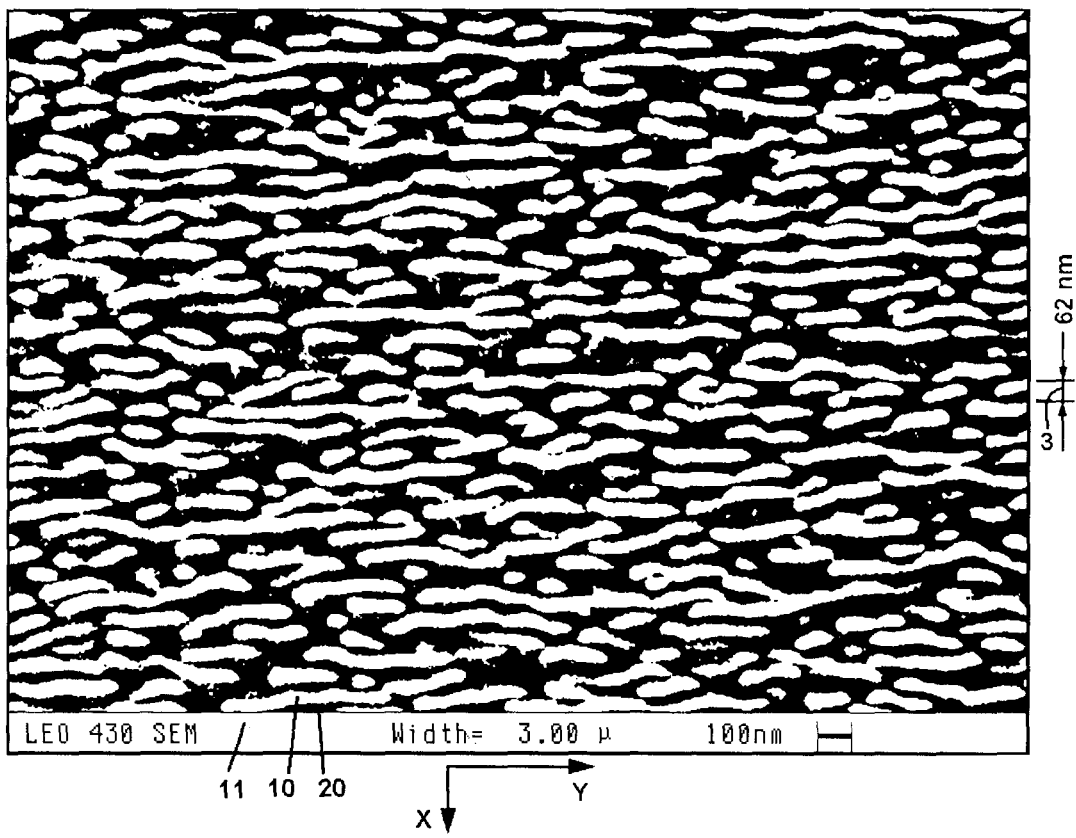
FIG. 1F is a SEM top view of a nanomask with a period of 62 nm formed on a surface of a silicon wafer using a $N_2^+$ ion beam at E=2 keV, θ=63°, according to the invention.
Figure 1G:
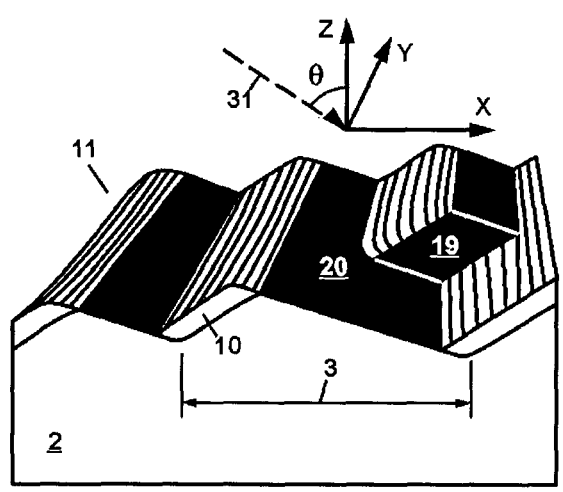
FIG. 1G is a perspective view of elongated elements of a nanomask and their cross-section, according to the invention.

FIGS. 1D to 1F show a nanomask 1 with a topology characterized in that regions are mostly separated from each other and regions 20 are mostly connected to each other in a continuous net. Nanomask 11 is formed by irradiation using a $N_2^+$ beam at greater angles of ion incidence relative to the silicon surface (e.g., angles of about $\theta=60°$-$65°$.) The cross-section of the elements of nanomask 11, as shown in FIG. 1G, are characterized in that regions 10 are mostly tilted relative to the array XY plane at a larger angle than regions 20. The slope of regions 10 is about $25°$-$30°$, and the slope of regions 20 is about $30°$-$35°$ relative to the array plane. End surfaces of typical wave breaks 19 were irradiated by the beam of nitrogen ions at grazing angles of about $70°$ or more, therefore they are the same thickness as regions 20 and connect regions 20 in a continuous mesh. Wave breaks 19 also occur in nanomask 1.

Figure 1H:
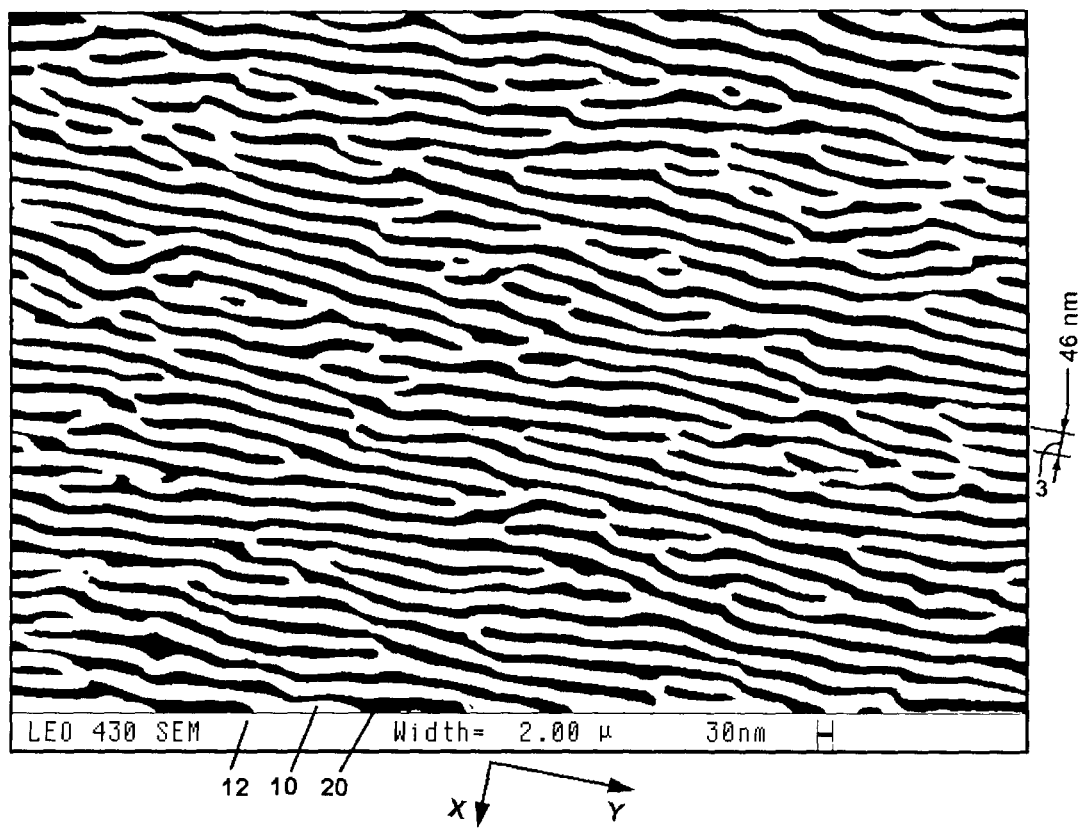
FIG. 1H is a SEM top view of a nanomask with a period of 46 nm formed on a surface of a silicon wafer using a $N_2$ ion beam at E=2 keV, θ=43°, according to the invention.
Figure 1I:
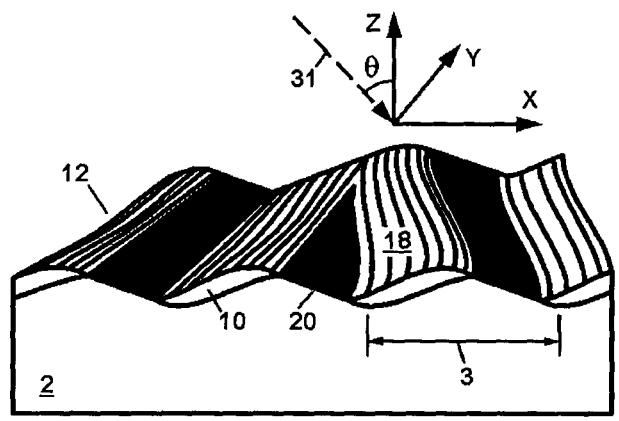
FIG. 1I is a perspective view of elongated elements of a nanomask and their cross-section, according to the invention.

FIG. 1H shows a nanomask 12 with a topology characterized in that regions 10 are mostly connected to each other in a continuous mesh and regions 20 are mostly separated from each other. Nanomask 12 is formed by irradiation using a $N_2^+$ beam at angles of ion incidence relative to the silicon surface of about $\theta=42°$-$45°$. The cross-section of elements of nanomask 12, as shown in FIG. 1I, is characterized in that regions are generally tilted relative to the array XY plane at a smaller angle than regions 20. The slope of regions 10 is about $25°$-$30°$, and the slope of regions 20 is about $30°$-$35°$ relative to the array plane. The surfaces of typical joints of waves 18 were irradiated by nitrogen ion beam at an angle of less than $30°$, therefore they are the same thickness as regions 10, and regions 18 connect regions 10 in a continuous mesh. The thickness of regions 18 is slightly smaller than the thickness of regions 10 located parallel to the Y-axis. Wave joints 18 are also seen in nanomasks 1 and 11. Wave breaks 19 also occur in nanomask 12.

It should be noted that in FIGS. 1A to 1I the WOS-nanomasks are shown at the final stage of wave amplitude growth at the sputtering depth $D_F$. In such nanomasks with grown (saturated) wave amplitudes the regions 20 are not formed in all cases, for example, they may be absent for large grazing angles of ion incidence $\theta>65°$ to the initial silicon surface, and when $\theta=45°$-$65°$ the formation of silicon nitride in regions may require their relaxation in vacuum for tens of minutes or exposure to air. In contrast, for WOS-nanomasks at the stage of wave amplitude growth, at the sputtering depth $d$ ($D_m<d<D_F$), both regions 10 and regions 20 are formed, and during the increase in wave amplitude the thickness of regions 10 increases and the thickness of regions 20 decreases. Pronounced periodic changes in the thickness of regions 10 along the nanomask elements are characteristic only for the grown waves. During further sputtering, especially at sputtering depths $>3D_F$, along with the increase in period of WOS-nanomask the periodic changes in the thickness of regions 10 along the nanomask elements weaken. Thus, both the regions 20 and the periodic changes in the thickness of regions 10 along the nanomask elements are not obligatory features of the nanomask, and may develop only under particular conditions.

FIG. 2A shows schematically transformation stages of a nanomask 1 during an RIE process for the formation of a nanostructured surface with a quasiperiodic array of silicon nanoridges with sawtooth cross-section. If desired, prior to the main RIE stage, ultra-thin regions 20 (<0.5 nm) between nitride regions 10 are removed from the initial structure 400 to form structure 401, thus enhancing the contrast of the nanomask 1. In one example, this process takes about 2 seconds and may allow one to significantly accelerate the etching of nanomask 1. The removal can be carried out in, for example, a non-selective plasma $He/CHF_3$ or in the selective plasma $O_2/Cl_2$ of the main RIE stage. In the latter case, the bias on the wafer under etching can be briefly raised, which provides a mode for ion sputtering of regions 20. As a result the nanomask 401 is formed without regions 20. Regions 20 can also be removed by wet etching in $HNO_3/HF$ solution for a few seconds. When the RIE process is implemented immediately after the formation of the WOS-nanomask without its exposure in air the step of removing regions 20 may not be performed, because these regions often do not occur.

The main RIE stage includes etching silicon in, for example, a chlorine $O_2/Cl_2$ plasma that is selective to nitride resulting sequentially in the structures 402-405. The main RIE stage takes, for example, 20 seconds, which provides a potential for high process productivity. Initially, during the etching of silicon 2 in the structure 402 the walls of the trenches between the regions 10 of silicon nitride are etched vertically. The etching process results in gradual decrease in the thickness of regions 10 of silicon nitride and these regions 10 transform into regions 10a and 10b. The walls of the trenches become inclined resulting in the structures 403 and 404. The flow of plasma ions reflected down from the walls of the trenches sharpens the trench bottoms. After the complete removal of the nanomask, i.e. regions 10b, the structure shape tends to a triangular profile as in the structure 405 with a quasiperiodic array of nanoridges 24 of silicon with a sawtooth cross-section. Array period 3 coincides with the period of nanomask 1. In at least some embodiments, the height 25 of nanoridges 24 is essentially the same for all nanoridges in the array. The ratio of nanoridge height 25 to the array period 3 may be in the range, for example, from 2 to 3.

Some RIE modes can result in the structure 404a, which is shown in FIG. 2B. In these modes silicon or silicon containing compounds such as silicon oxide, silicon oxychloride, silicon oxybromide, silicon oxyfluoride, or other compounds, which are the products of silicon etching in plasma of different compositions, can diffuse on the tops of ridge elements, on their sidewalls, or deposit onto these tops from plasma gases with the formation of regions 8. The tops of regions 8 in cross-section can be M-shaped as in the structure 404a or rounded. In case of a fragmented wavelike nanomask, regions 9 and 9a, shown in FIGS. 9C and 9D, respectively, can be formed as a result of RIE. Thus, the bases of the ridge elements can be made of elongated silicon elements 23a or shortened silicon elements 30b and the tops can be made up of regions 8, 9 or 9a. In this case, the ratio of the height 25 of the ridge elements to the array period 3 can be enlarged, for example, in the range from 3 to 5.

FIG. 2C shows a transformation of the wavelike nanomask during a wet etching process which selectively etches silicon with respect to silicon nitride in, for example, a solution of $HNO_3/HF$ (250:1 (v/v)). The etching may take, for example, 11 seconds. First, the regions 20 are removed (in instances in which these regions have been formed) to provide the structure 411 with shallow trenches between silicon nitride regions 10. Due to limited selectivity the size of regions 10 of silicon nitride is gradually decreased and the regions 10 transform into the regions 10c and 10d on the tops of silicon ridge elements 23b and 23c in structures 412 and 413, respectively. The isotropic nature of wet etching may result in side underetching of the ridge elements 23c and the formation of hung edges of regions 10d. The ratio of the nanostructure height 25a to the array period 3 can reach, for example, 0.5 to 0.9.

FIGS. 3A to 3D and 4A to 4B show arrays of nanoridges formed from nanomasks 1 with the same topology but with different periods. Arrays of nanoridges with average periods of 85, 53, 36, and 30 nm were obtained by RIE from nanomasks 1 with the same corresponding periods. Nanomasks were obtained by the bombardment of areas of silicon wafers by a nitrogen ion beam $N_2^+$ at angle $\theta=53°$ with energies of 5, 4, 2, and 1.5 keV, respectively. With the decreasing period of nanomask 1 the topology of the arrays of nanoridges significantly changes from the topology of regions 10 in nanomask 1 to an array of separated nanopeaks.

Figure 3A:
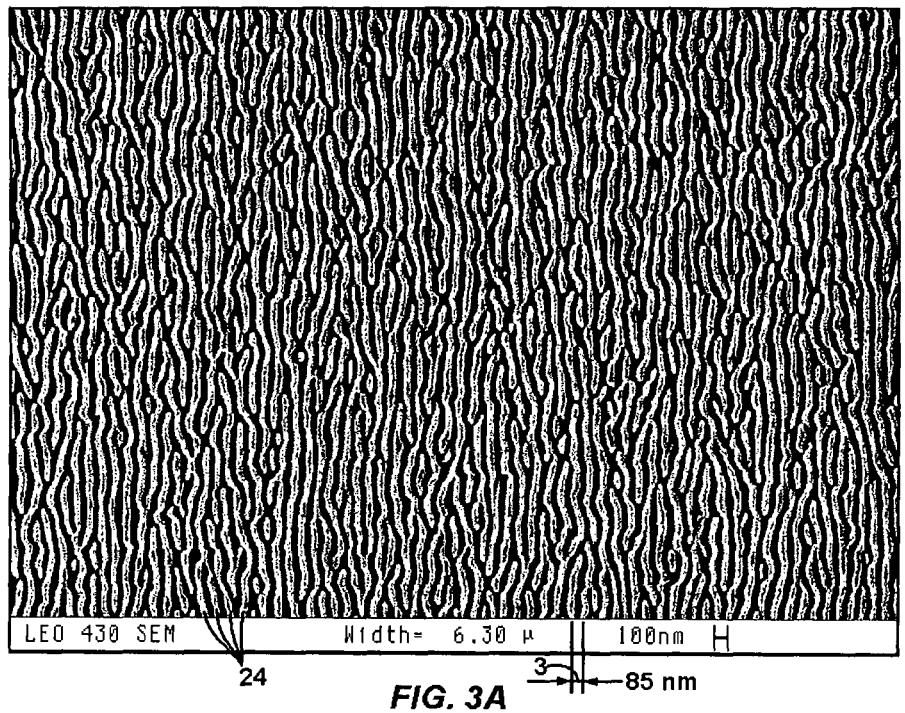
FIGS. 3A to 3D are SEM top views of quasiperiodic arrays of silicon nanoridges having a sawtooth cross-section with different periods of 85, 53, 36, and 30 nm, respectively, according to the invention.

An SEM image (top view) of an array of elongated nanoridges with an average period of 85 nm is shown in FIG. 3A. The tops of the nanoridges (the middles of light stripes 24) are displayed in the SEM as dark threads. This feature is related to a specific SEM instrument LEO 430, the maximum resolution of which is achieved at a high energy of electrons of 30 keV. In the case of low-voltage SEM the tops of the nanoridges are seen as bright. From this SEM image one can see that the nanoridges are elongated in the plane of the array and substantially oriented in one direction, i.e., along the vertical edges of the image, some nanoridges connecting to the neighboring nanoridges and forming branched structures.

Figure 3B:
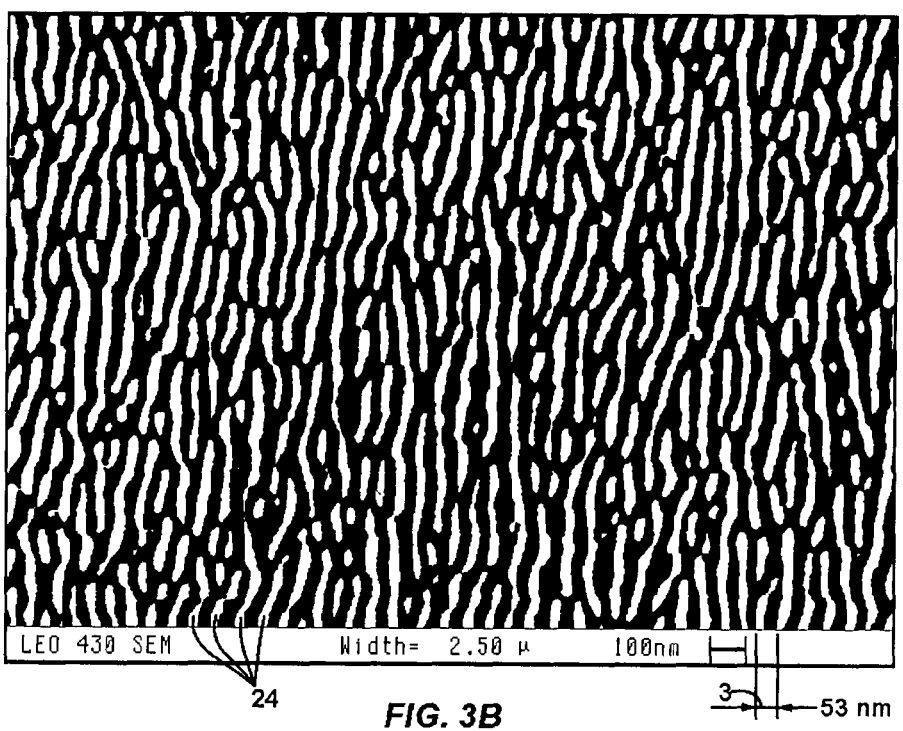

An SEM image (top view) of an array of elongated nanoridges with an average period of 53 nm is shown in FIG. 3B. The tops of the nanoridges 24 are shown in the SEM as white stripes. It is seen that with decreasing period the topology of the array of nanoridges changes. As in the previous case the nanoridges are elongated in the plane of the array and substantially oriented in one direction, but now the nanoridges are mostly separated from each other.

Figure 3C:
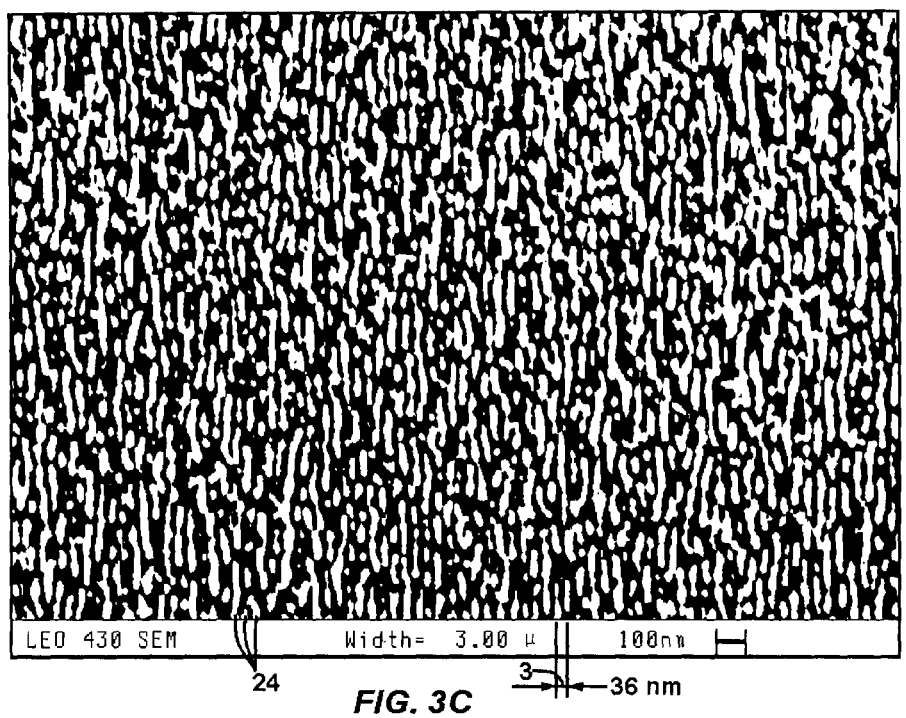

With further decrease in the period of the array of nanoridges down to 36 nm an increasing number of separated nanopeaks are observed as shown in FIG. 3C. In this case, however, the unidirectional orientation of the nanoridges is obvious, because most of them have an elongated shape.

Figure 3D:
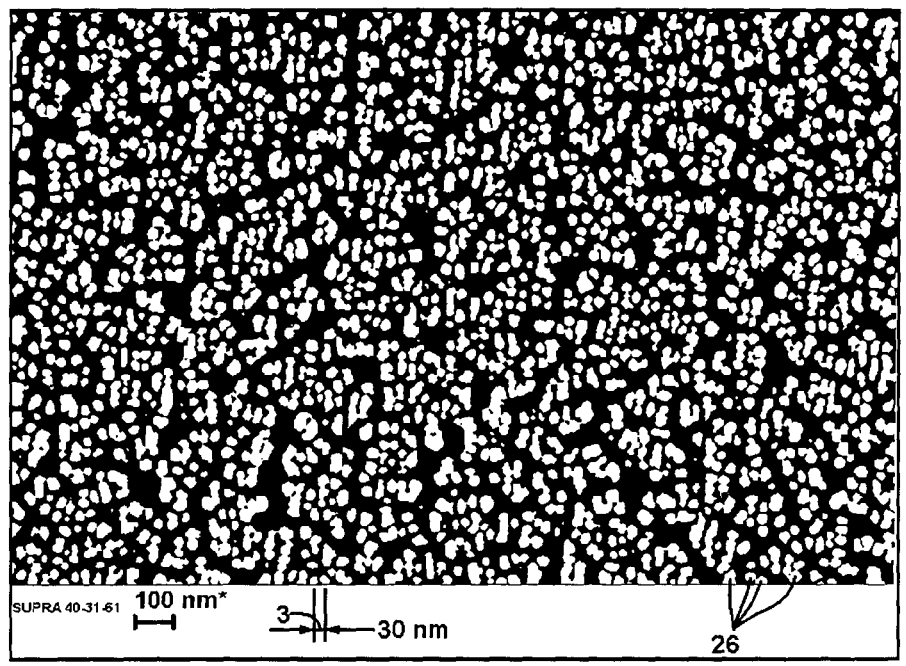

When the period of the array of nanoridges reaches 30 nm, the pattern significantly changes. Now the array mainly consists of separated nanopeaks 26, some of which are arranged as quasiperiodic rows, as shown in FIG. 3D. The arrangement of the quasiperiodic rows is determined by the pattern of regions 10 of the nanomask.

The observed change in the topology of the array of nanoridges may be caused by enhancement of a relative change in thickness of region 10 in the wavelike nanomask with a decrease in its period, which manifests itself in RIE modes having lower selectivity. In these RIE modes, for nanomasks with shorter periods in the range of 20 to 40 nm, the thinnest areas 4 of regions 10 are etched faster than thickest areas 5 (see, FIG. 1C), and as a result these nanomasks transform into chains or rows of separated nanopeaks. In RIE modes having relatively high selectivity the nanomask does not transform into the array of nanopeaks. These modes result in arrays of elongated nanoridges having the topology of the initial nanomask with periods in the range of 20 to 40 nm.

By lowering the selectivity of the RIE etching modes it is possible to obtain quasi-periodic rows of nanopeaks in the range of nanomask periods from 20 to 150 nm (or 20 to 180 nm or 20 to 200 nm).

Figure 4A:
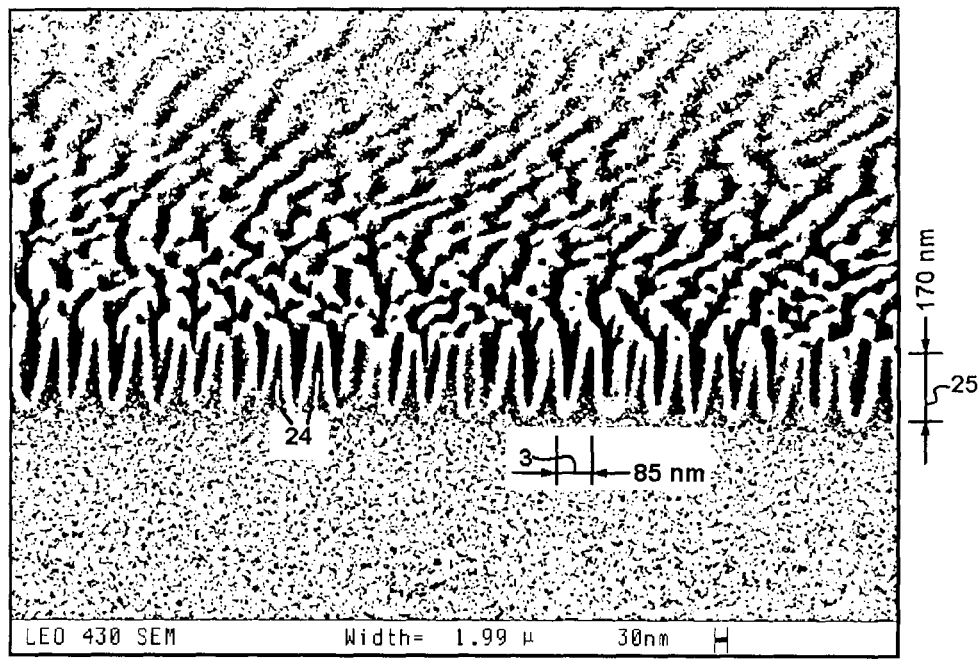
FIGS. 4A to 4B are SEM cross-sectional views, angled at 820, of quasiperiodic arrays of silicon nanoridges with periods of 85 and 53 nm, respectively, according to the invention.
Figure 4B:
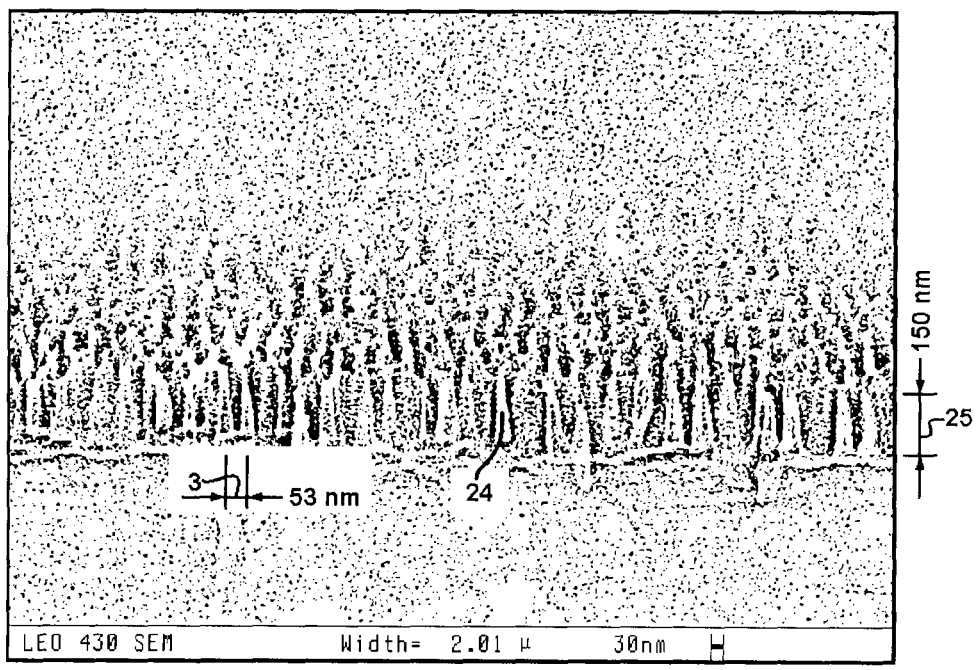

FIGS. 4A and 4B show cleft samples of silicon wafers with quasiperiodic arrays of silicon nanoridges with periods of 85 and 53 nm, respectively, and heights of the nanoridges in the arrays of about 170 and 150 nm, respectively. The ratio of nanoridge height 25 to the period 3 of the array in FIG. 4A is close to 2 and in FIG. 4B is close to 3.

Figure 8:
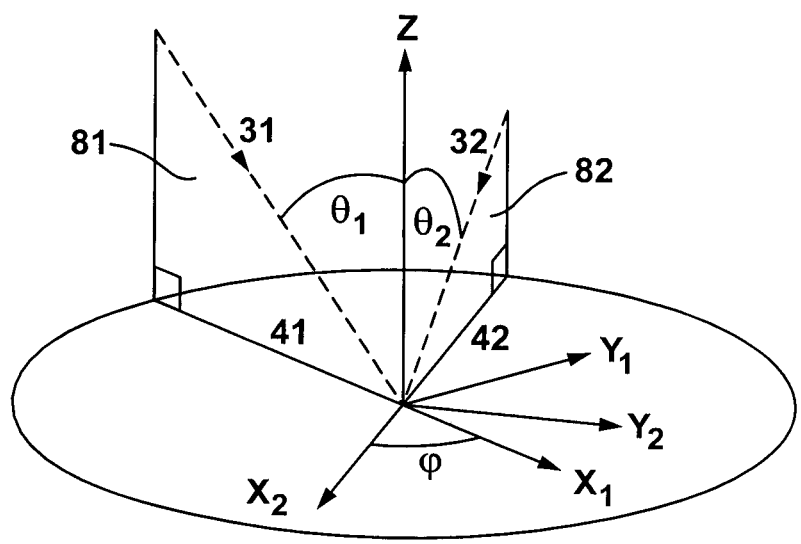
FIG. 8 is a diagram illustrating a mutual arrangement of ion fluxes to form a fragmented wave ordered structure.

FIG. 8 illustrates a mutual arrangement of the ion fluxes for forming fragmented wavelike nanomask as a result of a two stage process. At the first stage a first irradiation of the surface of a wafer is performed with a flux of nitrogen ions in the first plane 81 of incidence of the nitrogen ions to form a primary nanomask. The plane 81 coincides with the $ZX_1$-plane of the rectangular coordinate system $ZX_1Y_1$. In this arrangement the flux of nitrogen ions is directed along the arrow 31 and the projection 41 of the ion flux onto the surface of the wafer is directed along the $X_1$-axis. The primary nanomask has a quasi-periodic, anisotropic array of elongated elements with a wave-ordered structure pattern and a wave-like cross-section with wave crests that are substantially aligned along the $Y_1$-axis, i.e., perpendicular to the first plane 81 of incidence of the nitrogen ions. Then at the second stage a second irradiation of the surface of the primary nanomask is performed with a flux of nitrogen ions in a second plane 82 of incidence of the nitrogen ions which is rotated around the wafer surface normal, i.e., the Z-axis, by an azimuthal angle $\phi$ with respect to the first plane 81 to form a secondary nanomask. The plane 82 coincides with the $ZX_2$-plane of the rectangular coordinate system $ZX_2Y_2$. At this second irradiation the flux of nitrogen ions is directed along the arrow 32 and the projection 42 of the ion flux onto the surface of the wafer is directed along the $X_2$-axis. The secondary nanomask has a quasi-periodic, anisotropic array of elongated elements with a wave-ordered structure pattern and a wave-like cross-section with wave crests that are substantially aligned along the $Y_2$-axis, i.e., perpendicular to the second plane 82 of incidence of the nitrogen ions.

In one example, the ion bombardment angles are $\theta_1=53°$ and $\theta_2=65°$, the azimuthal angle is $\phi=55°$, and the ion energy is the same at the first and at the second stages of the irradiation. In at least some embodiments, the azimuthal angle $\phi$ may be in the range 30 to 90 degrees. In at least some embodiments, the secondary nanomask can be a fragmented wave ordered structure, i.e., the nanomask has substantially separated elements, most of which have an elongation from $0.5\lambda$ to $3\lambda$, where $\lambda$ is the wavelength of the primary nanomask.

Examples of nanostructured surfaces of silicon wafers with a fragmented wavelike nanomask are shown in FIGS. 10A and 11A. The nanostructured surface of FIG. 10A is formed as a result of wet etching of the fragmented wavelike nanomask in a solution of $HF/HNO_3$ and the nanostructured surface of FIG. 11A is formed as a result of RIE of the fragmented wavelike nanomask in a $Cl_2/O_2$ plasma. In both cases the fragmented wavelike nanomask was formed as a result of a two stage process of ion irradiation. At the first stage the energy of $N_2$ ions was E=5 keV and bombardment angle $\theta=53°$. At the second stage E=5 keV, $O_2=65°$, and $\phi=55°$. The ion dose of the second stage was equal to that of the first stage.

Figure 12:
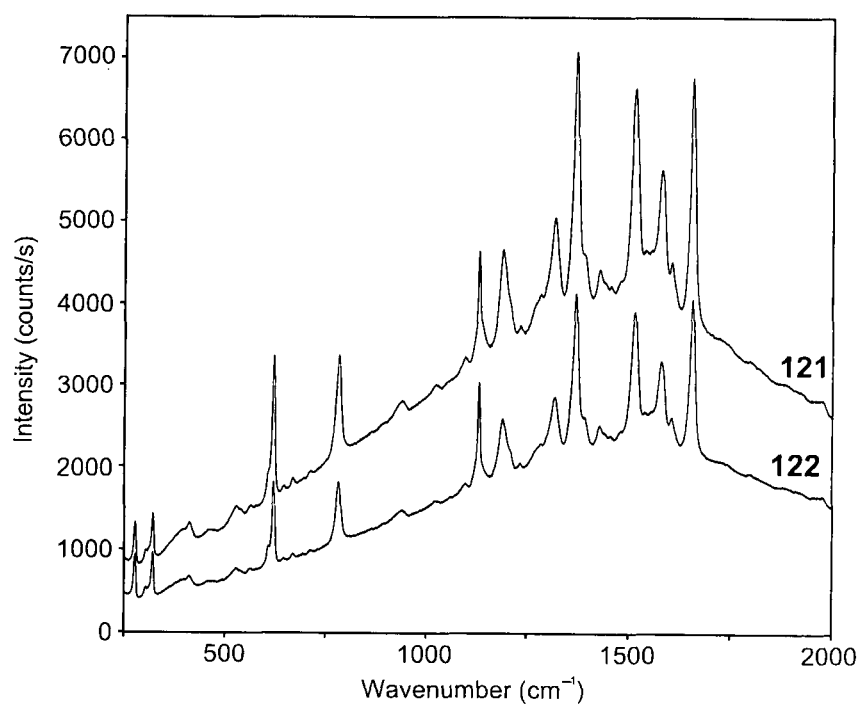
FIG. 12 is Raman spectra for rhodamine 6G (R6G) obtained from a surface of the SERS-sensor shown in FIGS. 6A and 6B, according to the invention.

FIG. 12 shows Raman spectra for rhodamine 6G (R6G) from the surface of the SERS-sensor shown in FIGS. 6A and 6B. The wavelength of the polarized exciting laser is 514.5 nm, the laser beam power is 70 MW, the laser beam diameter on the surface of the SERS-sensor is 2 μm, and the acquisition time for the spectra is 300 ms. This Raman detector is not sensitive to the light polarization. Rhodamine molecules were deposited on the SERS-sensor surface in an amount that is equivalent to one monolayer on a flat surface. The spectra of FIGS. 13 and 14 were recorded under the same conditions. The spectrum 121 (FIG. 12) corresponds to light polarized along the nanoridges on the sensor surface and the spectrum 122 (FIG. 12) corresponds to light polarized perpendicular to the nanoridges.

Figure 13:
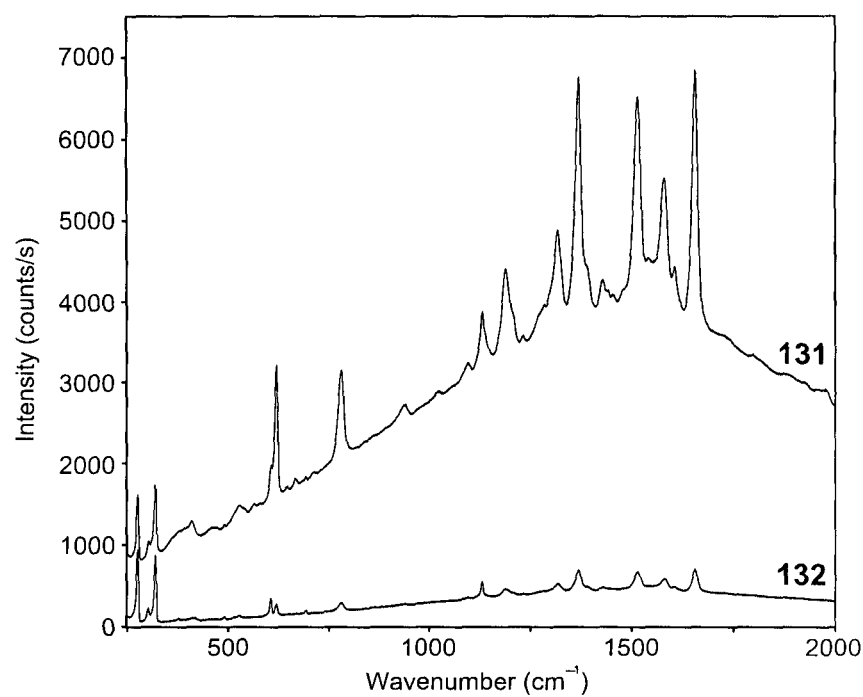
FIG. 13 is Raman spectra for rhodamine 6G (R6G) obtained from a surface of the SERS-sensor shown in FIG. 7A, according to the invention.

FIG. 13 shows Raman spectra for rhodamine 6G (R6G) from the surface of the SERS-sensor shown in FIG. 7A. The spectrum 131 corresponds to laser light polarized along the ridge elements and along the silver nanowires on the sensor surface, and the spectrum 132 corresponds to laser light polarized perpendicular to the nanowires. It is seen that a SERS-sensor with silver nanowires is sensitive to the polarization of the exciting light. The amplitudes of corresponding peaks in the spectra 131 and 132 differ by more than an order of magnitude.

Figure 14:
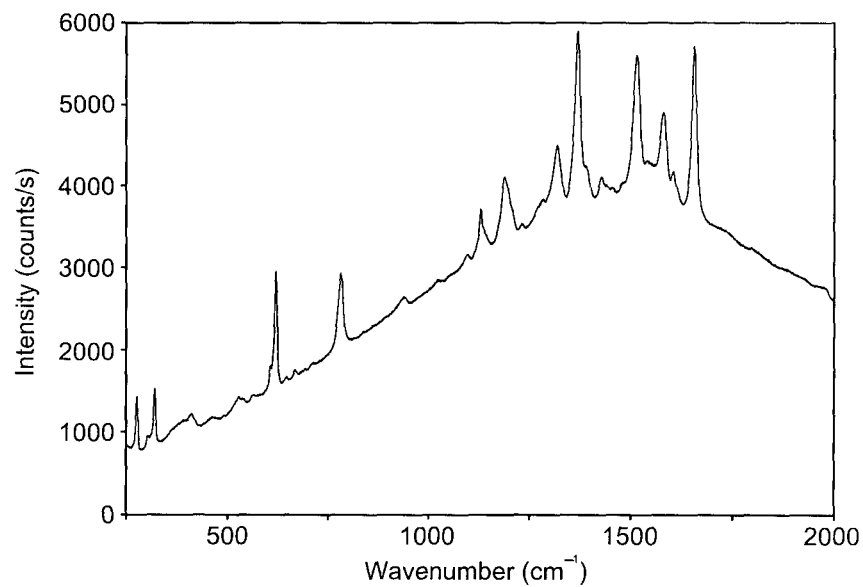
FIG. 14 is a Raman spectrum for rhodamine 6G (R6G) obtained from the surface of the SERS-sensor shown in FIG. 10B, according to the invention.

FIG. 14 shows a Raman spectrum for rhodamine 6G (R6G) from the surface of the SERS-sensor shown in FIG. 10B. This SERS-sensor, which has a nanostructured substrate surface with a fragmented wavelike structure, is almost insensitive to the polarization of the exciting light. The enhancement factor of this sensor is close to the enhancement of the SERS-sensor of FIG. 7A for the polarization of exciting light that is along silver nanowires.

Figure 15:
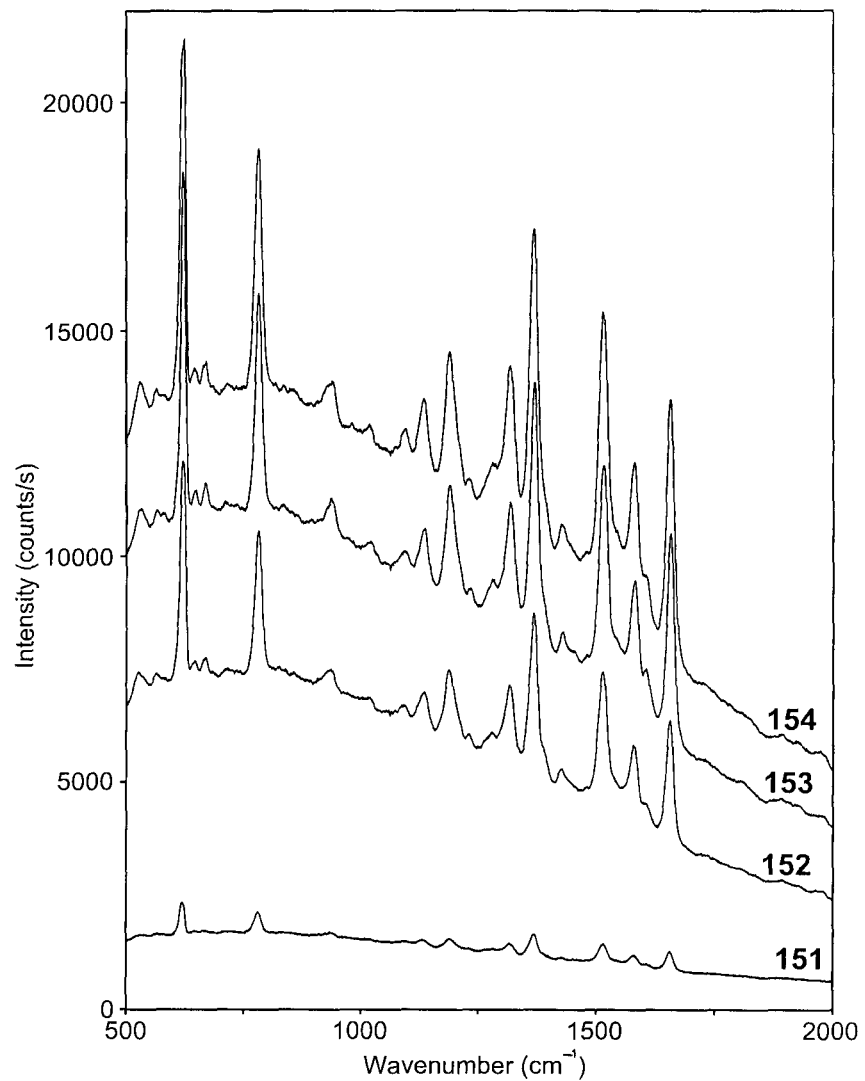
FIG. 15 is Raman spectra for rhodamine 6G (R6G) obtained from the surface of other embodiments of a SERS-sensor, according to the invention.
Figure 16A:
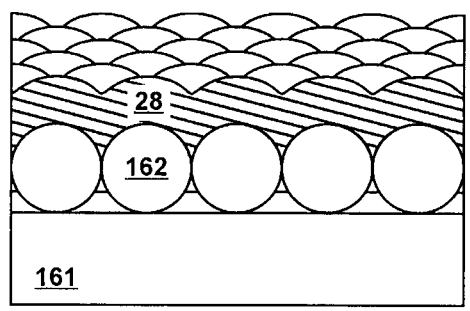
FIGS. 16A to 16B are schematic cross-sectional views of conventional SERS-sensors.
Figure 16B:
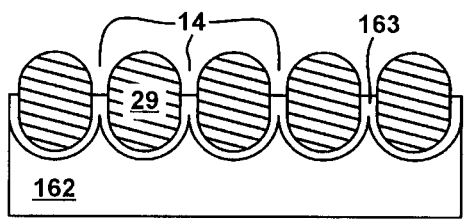

FIG. 15 shows Raman spectra for rhodamine 6G (R6G) from the surface of different embodiments of a SERS-sensor with excitation of depolarized laser light at a wavelength of 532.2 nm. Other parameters of spectra acquisition were kept unchanged. The spectrum 151 was recorded using the SERS-sensor shown in FIG. 7A. The spectrum 152 was recorded using a SERS-sensor having a nanostructure on the surface of solar silicon in the form of the array of nanoridges with a period of about 80 nm and a height of about 140 nm and a silver coverage with an equivalent-mass thickness of 208 nm. The spectrum 153 was recorded using the SERS-sensor shown in FIGS. 11B and 11C. The spectrum 154 was recorded using a SERS-sensor with a nanostructure on the silicon wafer surface, which is similar to that shown in FIG. 11A, i.e., corresponding to a fragmented nanomask, and with a mass-equivalent thickness of the silver coverage of 270 nm. The enhancement factor of SERS-sensors based on fragmented wavelike nanomask is evaluated as $5 \times 10^7$ for rhodamine. The enhancement of the SERS-sensors based on the array of elongated nanoridges shown in FIG. 3A is two times less for rhodamine.

Figure 17A:
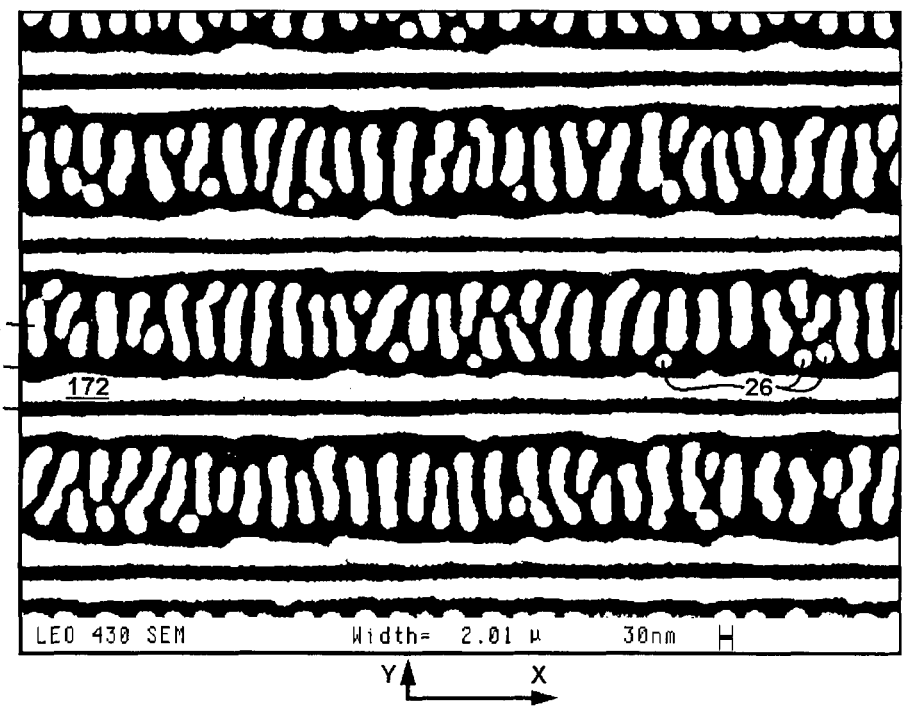
FIGS. 17A to 17C are SEM top views of quasiperiodic arrays of silicon ridge elements which are formed on a surface of a periodic grating, according to the invention.
Figure 17B:
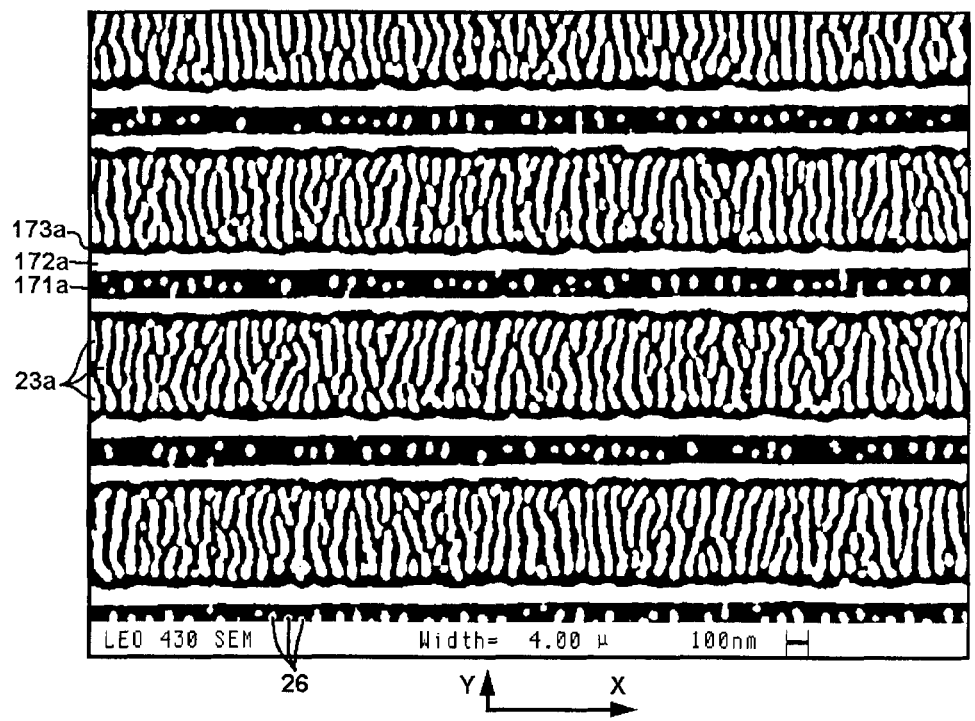
Figure 17C:
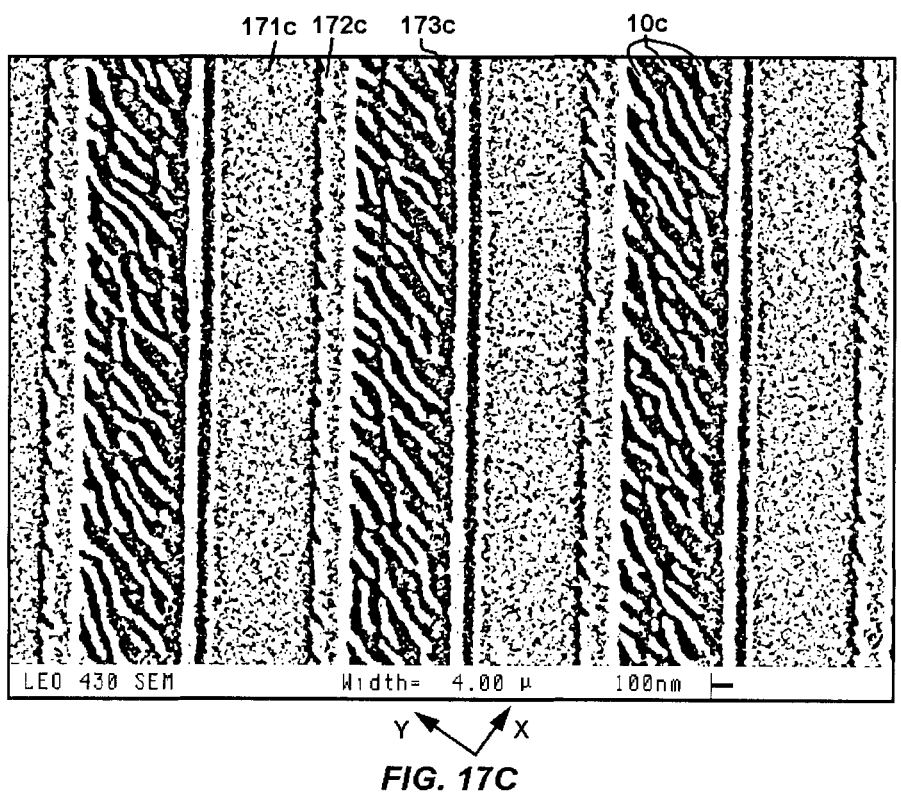

Examples of hybrid nanostructured surfaces, in which a self-forming nanopattern is combined with a lithographic pattern, are presented in FIGS. 17A to 17C. FIG. 17A shows an SEM top view of a nanostructured surface of a periodic grating with a rectangular surface profile. The grating period is 400 nm, the line and space width is 200 nm, and the grating profile depth is 200 nm. The wavelike nanomask was formed on the surface of silicon grating by irradiating the grating surface with nitrogen ions at E=5 keV, θ=53°, and with the ion flux projection on the grating surface being directed along the grating lines, i.e., along the X-axis. The nanomask period is about 70 nm. This nanostructured surface was formed as a result of RIE of silicon to the depth of about 200 nm. The nanostructured surface includes elongated ridge elements 23a which are aligned substantially perpendicular to the grating lines, nanopeaks 26, surface areas 173 between the elements 23a and 26 on tops of grating lines, narrow trench bottoms 171 between the grating lines, and inclined flat areas 172 which are formed from the vertical line sidewalls in the process of silicon sputtering under ion bombardment.

FIG. 17B shows an SEM top view of a nanostructured surface of a periodic grating with a rectangular surface profile. The grating period is 800 nm, the line and space width is 400 nm, and the grating profile depth is 200 nm. The wavelike nanomask was formed on the surface of silicon grating by irradiating the grating surface with nitrogen ions at E=5 keV, θ=53°, and with the ion flux projection on the grating surface being directed along the grating lines, i.e., along the X-axis. The nanomask period is about 70 nm. This nanostructured surface was formed as a result of RIE of silicon to the depth of about 200 nm. The nanostructured surface includes elongated ridge elements 23a, which are aligned substantially perpendicular to the grating lines, nanopeaks 26, which are located substantially on the trench bottoms 171a, surface areas 173a between the elements 23a on tops of grating lines and inclined flat areas 172a, which are formed from the vertical line sidewalls in the process of silicon sputtering under ion bombardment.

FIG. 17C shows an SEM top view of a nanostructured surface of a periodic grating with a rectangular surface profile. The grating period is 1.2 am, the line width is 0.74 μm, the space width is 0.56 μm, and the grating profile depth is 200 nm. The wavelike nanomask was formed on the surface of silicon grating by irradiating the grating surface with nitrogen ions at E=5 keV, θ=60°, and with the ion flux projection on the grating surface being directed at an angle 35° with respect to the grating lines, i.e., along the X-axis. The nanomask period is about 80 nm. This nanostructured surface was formed as a result of wet etching of silicon to the depth of about 40 nm. The nanostructured surface includes elongated regions 10c of nanomask of silicon nitride, which are aligned substantially along the Y-axis, the trench bottoms 171c, surface areas 173c between the elongated ridge elements on tops of grating lines, and inclined flat areas 172c, which are formed from the vertical line sidewalls in the process of silicon sputtering under ion bombardment.

Thus, the SERS-sensor having a substrate with a nanostructured surface can be fabricated in different ways in accordance with the present invention.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent is:

1. A surface enhanced Raman scattering (SERS) sensor, comprising
   a substrate with a nanostructured surface, the nanostructured surface comprising a quasi-periodic, anisotropic array of elongated ridge elements having a wave-ordered structure pattern, each ridge element having a wavelike cross-section and oriented substantially in a first direction, wherein formation of the quasi-periodic anisotropic array includes irradiating a surface of the substrate with a first oblique beam of nitrogen ions in a first plane of incidence of the nitrogen ions to form a primary nanomask, irradiating the surface of the primary nanomask with a second oblique beam of nitrogen ions in a second plane of incidence of the nitrogen ions, the second plane being rotated around a normal of the substrate surface by an azimuthal angle with respect to the first plane, to form a secondary nanomask, the secondary nanomask comprising the quasi-periodic, anisotropic array of elongated ridge elements having the wave-ordered structure pattern and the wave-like cross-section with wave crests that are substantially perpendicular to the second plane of incidence of the nitrogen ions; and
   a plurality of metal elements disposed, at least in part, on tops of the ridge elements.

2. The SERS sensor of claim 1, wherein the substrate comprises silicon.

3. The SERS sensor of claim 1, wherein the anisotropic array has an average array period in a range from 20 to 200 nm.

4. The SERS sensor of claim 1, wherein a ratio of average height of the ridge elements to average period of the array is in a range from 0.5 to 5.

5. The SERS sensor of claim 1, wherein the metal elements form metal nanowires.

6. The SERS sensor of claim 1, wherein the metal elements comprise at least one metal selected from a group consisting of silver, gold, copper, platinum, palladium, rhodium, ruthenium, osmium, iridium, iron, cobalt, nickel, and aluminum.

7. The SERS sensor of claim 1, wherein at least one of the metal elements is a connected metal element extending, at least in part, over the tops of a plurality of the ridge elements.

8. The SERS sensor of claim 1, wherein the substrate defines a plurality of trenches between the ridge elements and wherein at least one of the metal elements extends to at least a bottom of a one of the trenches.

9. The SERS sensor of claim 1, wherein the azimuthal angle is in a range of 30 to 90 degrees.

10. The SERS sensor of claim 1, wherein the ridge elements have an "M"-shaped cross-section.

11. The SERS sensor of claim 1, wherein the ridge elements have a sawtooth cross-section.

12. A method of making a surface enhanced Raman scattering (SERS) sensor, the method comprising:
    irradiating a surface of a wafer with a first oblique beam of nitrogen ions in a first plane of incidence of the nitrogen ions to form a primary nanomask, the primary nanomask comprising a quasi-periodic, anisotropic array of elongated elements having a wave-ordered structure pattern and a wave-like cross-section with wave crests that are substantially perpendicular to the first plane of incidence of the nitrogen ions;
    irradiating the surface of the primary nanomask with a second oblique beam of nitrogen ions in a second plane of incidence of the nitrogen ions, the second plane being rotated around a normal of the wafer surface by an azimuthal angle with respect to the first plane, to form a secondary nanomask, the secondary nanomask comprising a quasi-periodic, anisotropic array of elongated elements having a wave-ordered structure pattern and a wave-like cross-section with wave crests that are substantially perpendicular to the second plane of incidence of the nitrogen ions; and
    etching the surface of the wafer with the primary nanomask to generate a nanostructured surface corresponding to the primary nanomask.

13. The method of claim 12, further comprising depositing metal elements over the nanostructured surface.

14. The method of claim 13, wherein depositing metal elements comprises forming metal nanowires on tops of the elongated elements.

15. The method of claim 13, wherein depositing metal elements comprises forming metal elements on, at least in part, tops of the elongated elements, wherein at least one of the metal elements is a connected metal element extending, at least in part, over the tops of a plurality of the ridge elements.

16. The method of claim 13, wherein the metal elements comprise at least one metal selected from a group consisting of silver, gold, copper, platinum, palladium, rhodium, ruthenium, osmium, iridium, iron, cobalt, nickel, and aluminum.

17. The method of claim 12, wherein the azimuthal angle is in a range from 30 to 90 degrees.

18. The method of claim 12, further comprising depositing metal elements over the nanostructured surface.

19. The method of claim 12, wherein the ridge elements have an "M"-shaped cross-section.

20. A nanostructured arrangement, comprising
    a substrate with a nanostructured surface, the nanostructured surface comprising a quasi-periodic, anisotropic array of elongated ridge elements having a wave-ordered structure pattern, each ridge element having a wavelike cross-section and oriented substantially in a first direction;
    wherein the wave-ordered structure pattern is a fragmented wave-ordered structure pattern formed by sequential ion irradiation along two different planes of ion incidence separated by an azimuthal angle in a range of 30 to 90 degrees, wherein formation of the wave-ordered structure pattern includes irradiating a surface of the substrate with a first oblique beam of nitrogen ions in a first plane of incidence of the nitrogen ions to form a primary nanomask, irradiating the surface of the primary nanomask with a second oblique beam of nitrogen ions in a second plane of incidence of the nitrogen ions, the second plane being rotated around a normal of the substrate surface by the azimuthal angle with respect to the first plane, to form a secondary nanomask, the secondary nanomask comprising the quasi-periodic, anisotropic array of elongated ridge elements having the wave-ordered structure pattern and the wave-like cross-section with wave crests that are substantially perpendicular to the second plane of incidence of the nitrogen ion.

* * * * *